(12) United States Patent
Zhang et al.

(10) Patent No.: US 12,064,290 B2
(45) Date of Patent: Aug. 20, 2024

(54) HARDSTOP DETECTION AND HANDLING FOR SURGICAL TOOL

(71) Applicant: Verb Surgical Inc., Santa Clara, CA (US)

(72) Inventors: Xiaobin Zhang, Santa Clara, CA (US); Renbin Zhou, Santa Clara, CA (US); Alireza Hariri, Santa Clara, CA (US)

(73) Assignee: Verb Surgical Inc., Santa Clara, CA (US)

( * ) Notice: Subject to any disclaimer, the term of this patent is extended or adjusted under 35 U.S.C. 154(b) by 484 days.

(21) Appl. No.: 17/498,988

(22) Filed: Oct. 12, 2021

(65) Prior Publication Data

US 2023/0112334 A1  Apr. 13, 2023

(51) Int. Cl.
*A61B 90/00* (2016.01)
*A61B 34/00* (2016.01)
*A61B 34/35* (2016.01)

(52) U.S. Cl.
CPC .............. *A61B 90/06* (2016.02); *A61B 34/35* (2016.02); *A61B 34/71* (2016.02); *A61B 2034/715* (2016.02); *A61B 2090/066* (2016.02)

(58) Field of Classification Search
CPC ........ A61B 2034/305; A61B 2034/715; A61B 2090/031; A61B 2090/035; A61B 2090/064; A61B 2090/066; A61B 34/35; A61B 34/37; A61B 34/71; A61B 90/06
See application file for complete search history.

(56) References Cited

U.S. PATENT DOCUMENTS

| 2018/0214219 A1 | 8/2018 | Overmyer et al. |
| 2019/0274769 A1 | 9/2019 | Perdue et al. |
| 2021/0146539 A1 | 5/2021 | Tanaka et al. |

FOREIGN PATENT DOCUMENTS

| WO | 2019164856 A1 | 8/2019 |
| WO | 2020118149 A1 | 6/2020 |

OTHER PUBLICATIONS

International Search Report and Written Opinion for International Application PCT/IB2022/058649 mailed Jan. 2, 2023.

*Primary Examiner* — Scott Luan
(74) *Attorney, Agent, or Firm* — Lempia Summerfield Katz LLC

(57) ABSTRACT

The disclosed embodiments relate to systems and methods for a surgical tool or a surgical robotic system. One example system for detecting a hardstop for a surgical tool includes a wrist connected to and driven by a plurality of cables of a tool driver, a plurality of sensors configured to detect forces associated with the plurality of cables one or more processors configured to perform a comparison of the forces associated with the plurality of cables, selected a highest tension cable from the plurality of cables based on the comparison of the forces associated with the plurality of cables, set a force assigned to the highest tension cable to a predetermined value, calculate a variable torque threshold for the wrist based on a sum of the predetermined value for the highest tension cable and detected forces for remaining cables in the plurality of cables, receive a joint torque value for the wrist, perform a comparison of the received joint torque value for the wrist to a variable wrist torque threshold and identify a hardstop based on the comparison of the received joint torque value for the wrist to the variable wrist torque threshold.

20 Claims, 11 Drawing Sheets

HARDSTOP DETECTION AND HANDLING FOR SURGICAL TOOL

FIELD

This disclosure relates to hardstop detection and handling during operation of a surgical tool.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more surgical tools (e.g., end effectors and endoscope) through the incisions into the patient. The surgical procedures may then be performed using the introduced surgical tools, with the visualization aid provided by the endoscope.

Generally, MIS provides multiple benefits, such as reduced patient scarring, less patient pain, shorter patient recovery periods, and lower medical treatment costs associated with patient recovery. Recent technology development allows more MIS to be performed with robotic systems that include one or more robotic arms for manipulating surgical tools based on commands from a remote operator. A robotic arm may, for example, support at its distal end various devices such as surgical end effectors, imaging devices, cannulae for providing access to the patient's body cavity and organs, etc. In robotic MIS systems, it may be desirable to establish and maintain high positional accuracy for surgical instruments supported by the robotic arms.

In some example, the surgical end effectors may contact a hardstop in the body or elsewhere. The hardstop may be a part of the body or another substantially rigid object that the end effector contacts. While some systems provide feedback to the user regarding contact with a hardstop, other systems may provide no feedback or only video. It may be impossible to identify the hardstop with no feedback and difficult to identify the hardstop with only video. The following disclosure provides a system, apparatus, and method for the identification of hardstops and handling of hardstops by a surgical tool.

SUMMARY

Disclosed herein is a robotically assisted surgical electromechanical system designed for surgeons to perform minimally invasive surgery. A suite of compatible tools can be attached/detached from an instrument driver mounted to the distal end of a robotic arm, enabling the surgeon to perform various surgical tasks. The instrument drivers can provide intracorporeal access to the surgical site, mechanical actuation of compatible tools through a sterile interface, and communication with compatible tools through a sterile interface and user touchpoints. The system detects an obstacle or hardstop experienced by the tool.

One apparatus for detecting a hardstop for a surgical tool comprises a wrist connected to and driven by a plurality of cables of a tool driver, a plurality of sensors configured to detect forces associated with the plurality of cables one or more processors configured to perform a comparison of the forces associated with the plurality of cables, selected a highest tension cable from the plurality of cables based on the comparison of the forces associated with the plurality of cables, set a force assigned to the highest tension cable to a predetermined value, calculate a variable torque threshold for the wrist based on a sum of the predetermined value for the highest tension cable and detected forces for remaining cables in the plurality of cables, receive a joint torque value for the wrist, perform a comparison of the received joint torque value for the wrist to a variable wrist torque threshold and identify a hardstop based on the comparison of the received joint torque value for the wrist to the variable wrist torque threshold.

DETAILED DESCRIPTION

Figure 1:
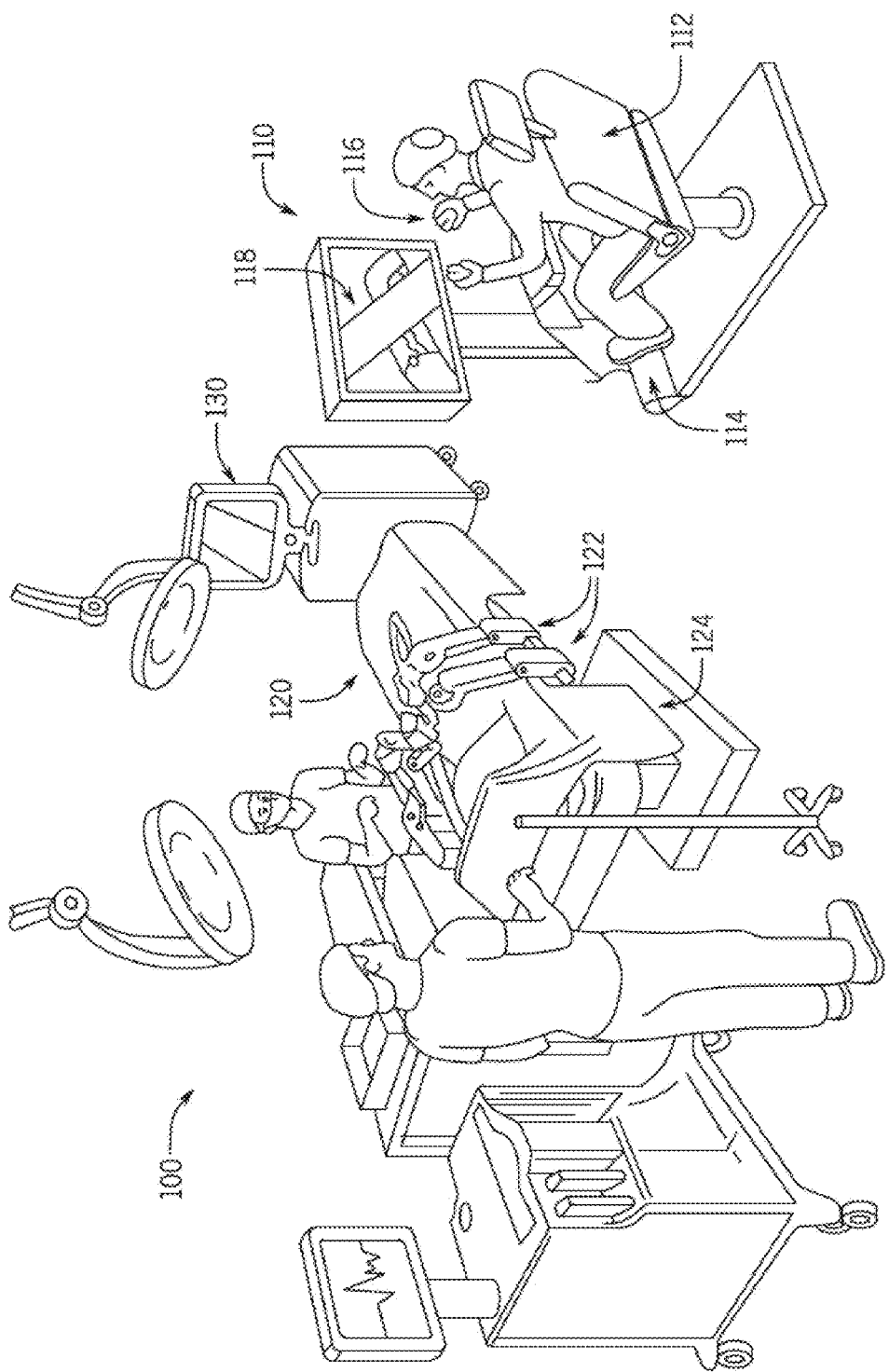
FIG. 1 illustrates an example operating room environment including a surgical robotic system.

FIG. 1 is a diagram illustrating an example operating room environment with a surgical robotic system 100. As shown in FIG. 1, the surgical robotic system 100 comprises a user console 110, a control tower 130, and a surgical robot 120 having one or more surgical robotic arms 122 mounted on a surgical platform 124 (e.g., a table or a bed etc.), where surgical tools with end effectors are attached to the distal ends of the robotic arms 122 for executing a surgical procedure. The robotic arms 122 are shown as table-mounted, but in other configurations, the robotic arms may be mounted in a cart, a ceiling, a sidewall, or other suitable support surfaces.

Generally, a user, such as a surgeon or other operator, may be seated at the user console 110 to remotely manipulate the robotic arms 122 and/or surgical instruments (e.g., teleoperation). The user console 110 may be located in the same operation room as the robotic system 100, as shown in FIG. 1. In other environments, the user console 110 may be located in an adjacent or nearby room, or teleoperated from a remote location in a different building, city, or country. The user console 110 may comprise a seat 112, pedals 114, one or more handheld user interface devices (UIDs) 116, and an open display 118 configured to display, for example, a view of the surgical site inside a patient. As shown in the exemplary user console 110, a surgeon sitting in the seat 112 and viewing the open display 118 may manipulate the pedals 114 and/or handheld user interface devices 116 to remotely control robotic arms 122 and/or surgical instruments mounted to the distal ends of the arms 122.

In some variations, a user may also operate the surgical robotic system 100 in an "over the bed" (OTB) mode, in which the user is at the patient's side and simultaneously manipulating a robotically-driven tool/end effector attached thereto (e.g., with a handheld user interface device 116 held in one hand) and a manual laparoscopic tool. For example, the user's left hand may be manipulating a handheld user interface device 116 to control a robotic surgical component, while the user's right hand may be manipulating a manual laparoscopic tool. Thus, in these variations, the user may perform both robotic-assisted minimally invasive surgery (MIS) and manual laparoscopic surgery on a patient.

An end effector may be configured to execute a surgical operation such as cutting, grasping, poking, or energy emission. The surgical tool may be manipulated manually, robotically, or both, during the surgery. For example, the surgical tool may be a tool used to enter, view, or manipulate an internal anatomy of the patient. In an embodiment, the surgical tool is a grasper that can grasp tissue of the patient. The surgical tool may be controlled manually, directly by a hand of a bedside operator or it may be controlled robotically, via sending electronic commands to actuate movement.

During an exemplary procedure or surgery, the patient is prepped and draped in a sterile fashion to achieve anesthesia. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 110 may utilize the pedals 114 and/or user interface devices 116 to manipulate various end effectors and/or imaging systems to perform the surgery. Manual assistance may also be provided at the procedure table by sterile-gowned personnel, who may perform tasks including but not limited to, retracting tissues or performing manual repositioning or tool exchange involving one or more robotic arms 122. Nonsterile personnel may also be present to assist the surgeon at the user console 110. When the procedure or surgery is completed, the robotic system 100 and/or user console 110 may be configured or set in a state to facilitate one or more post-operative procedures, including but not limited to, robotic system 100 cleaning and/or sterilization, and/or healthcare record entry or printout, whether electronic or hard copy, such as via the user console 110.

In some aspects, the communication between the surgical robot 120 and the user console 110 may be through the control tower 130, which may translate user input from the user console 110 to robotic control commands and transmit the control commands to the surgical robot 120. The control tower 130 may also transmit status and feedback from the robot 120 back to the user console 110. The connections between the surgical robot 120, the user console 110 and the control tower 130 may be via wired and/or wireless connections and may be proprietary and/or performed using any of a variety of data communication protocols. Any wired connections may be optionally built into the floor and/or walls or ceiling of the operating room. The surgical robotic system 100 may provide video output to one or more displays, including displays within the operating room, as well as remote displays accessible via the Internet or other networks. The video output or feed may also be encrypted to ensure privacy and all or portions of the video output may be saved to a server or electronic healthcare record system.

Prior to initiating surgery with the surgical robotic system, the surgical team can perform the preoperative setup. During the preoperative setup, the main components of the surgical robotic system (table 124 and robotic arms 122, control tower 130, and user console 110) are positioned in the operating room, connected, and powered on. The surgical platform 124 and robotic arms 122 may be in a fully-stowed configuration with the arms 122 under the surgical platform 124 for storage and/or transportation purposes. The surgical team can extend the arms from their stowed position for sterile draping.

After draping, the arms 122 can be partially retracted until needed for use. A number of conventional laparoscopic steps may be performed including trocar placement and installation. For example, each sleeve can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other trocars.

After insufflation, if required, manual instruments can be inserted through the sleeve to perform any laparoscopic steps by hand. Next, the surgical team may position the robotic arms 122 over the patient and attach each arm 122 to its corresponding sleeve. The surgical robotic system 100 has the capability to uniquely identify each tool (endoscope and surgical instruments) as soon as it is attached and display the tool type and arm location on the open or immersive display 118 at the user console 110 and the touchscreen display on the control tower 130. The corresponding tool functions are enabled and can be activated using the master UIDs 116 and foot pedals 114. The patient-side assistant can attach and detach the tools, as required, throughout the procedure. The surgeon seated at the user console 110 can begin to perform surgery using the tools controlled by two master UIDs 116 and foot pedals 114. The system translates the surgeon's hand, wrist, and finger movements through the master UIDs 116 into precise real-time movements of the surgical tools. Therefore, the system constantly monitors every surgical maneuver of the surgeon and pauses instrument movement if the system is unable to precisely mirror the surgeon's hand motions. In case the endoscope is moved from one arm to another during surgery, the system can adjust the master UIDs 116 for instrument alignment and continue instrument control and motion. The foot pedals 114 may be used to activate various system modes, such as endoscope control and various instrument functions including monopolar and bipolar cautery, without involving surgeon's hands removed from the master UIDs 116.

The surgical platform 124 can be repositioned intraoperatively. For safety reasons, all tooltips should be in view and under active control by the surgeon at the user console 110. Instruments that are not under active surgeon control are removed, and the table feet are locked. During table motion, the integrated robotic arms 122 may passively follow the table movements. Audio and visual cues can be used to guide the surgery team during table motion. Audio cues may include tones and voice prompts. Visual messaging on the displays at the user console 110 and control tower 130 can inform the surgical team of the table motion status.

Figure 2:
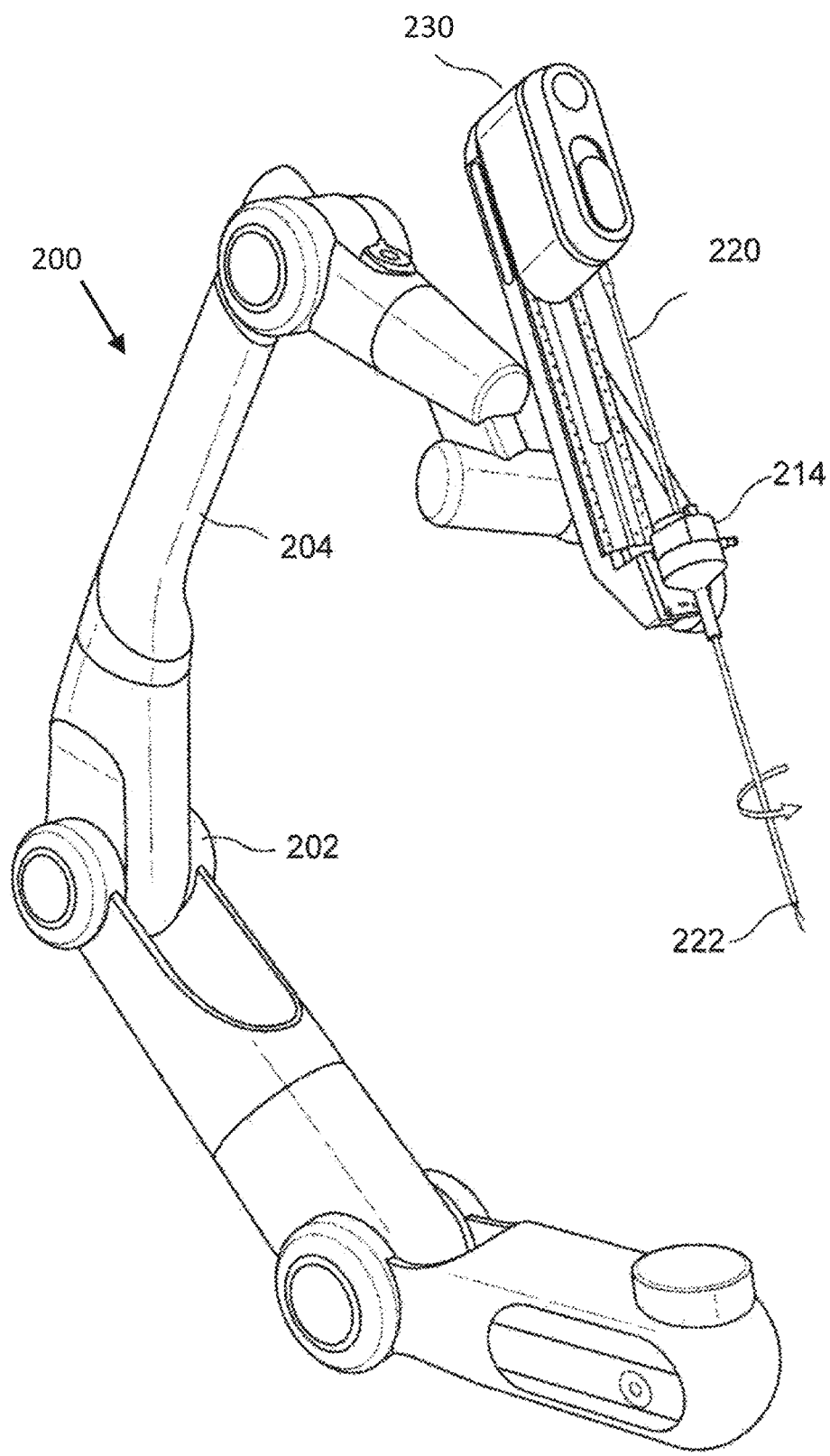
FIG. 2 illustrates an example surgical robotic system including a robotic arm, a tool driver, and a cannula loaded with a surgical tool.

FIG. 2 is a schematic diagram illustrating one exemplary design of a robotic arm, a tool driver, and a cannula loaded with a robotic surgical tool. As shown in FIG. 2, the example surgical robotic arm 200 may include a plurality of links (e.g., a link 202) and a plurality of actuated joint modules (e.g., a joint 204) for actuating the plurality of links relative to one another. The joint modules may include various types, such as a pitch joint or a roll joint, which may substantially constrain the movement of the adjacent links around certain axes relative to others. Also shown in the exemplary design of FIG. 2 is a tool driver 230 attached to the distal end of the robotic arm 200. The tool driver 230 may include a cannula 214 coupled to its end to receive and guide a surgical instrument (e.g. such as endoscopes, staplers, etc.). The surgical instrument 220 (or "tool") may include an end effector 222 at the distal end of the tool 220. The plurality of the joint modules of the robotic arm 200 can be actuated to position and orient the tool driver 230, which actuates the tool 220 for robotic surgeries.

Figure 3A:
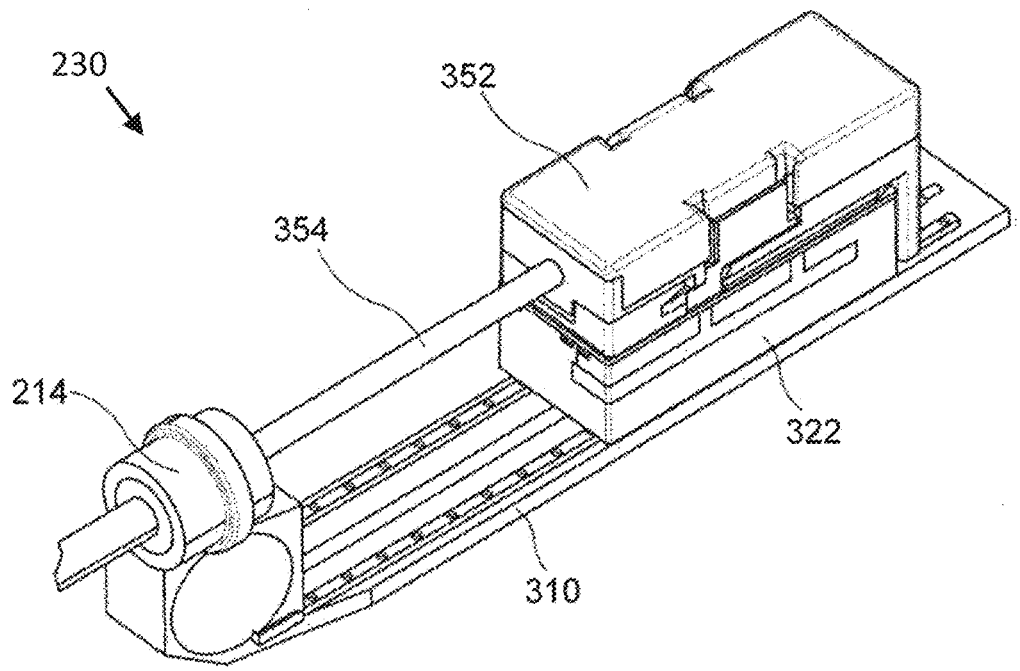
FIG. 3A illustrates an exemplary tool driver with a loaded surgical tool.
Figure 3B:
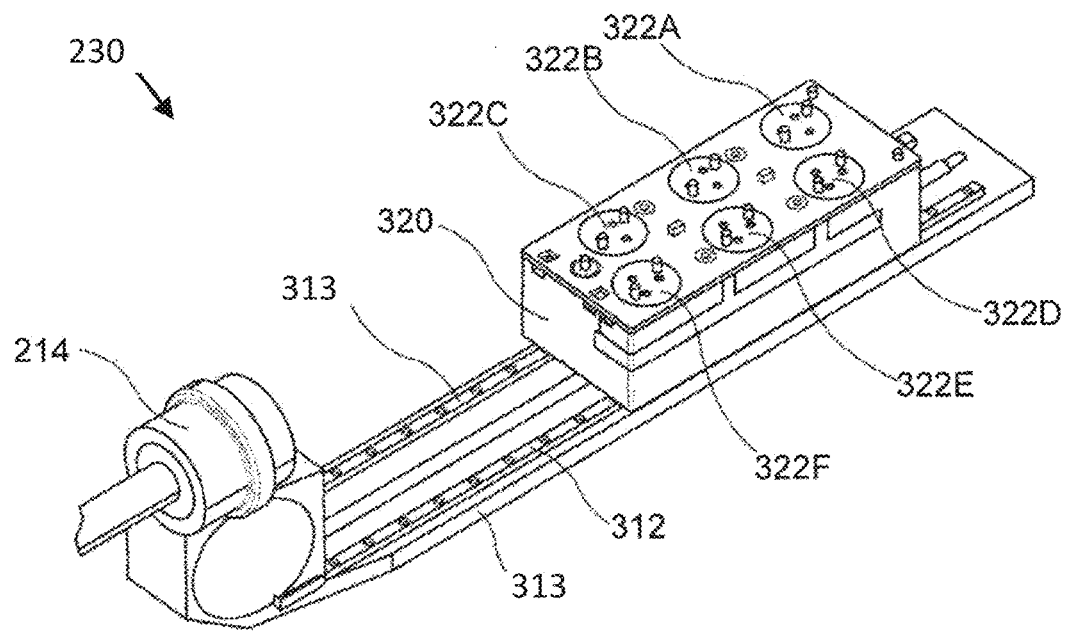
FIG. 3B illustrates an exemplary tool driver without a loaded surgical tool.

FIGS. 3A and 3B are schematic diagrams illustrating an exemplary tool driver with and without a loaded tool adjacent, respectively, in accordance with aspects of the subject technology. As shown in FIGS. 3A and 3B, in one variation, the tool driver 230 may include an elongated base (or "stage") 310 having longitudinal tracks 313 and a tool carriage 320, which is slidingly engaged with the longitudinal tracks 313. The stage 310 may be configured to couple to the distal end of a robotic arm such that articulation of the robotic arm positions and/or orients the tool driver 230 in space. Additionally, the tool carriage 320 may be configured to receive a tool base 352 of the tool, which may also include a tool shaft 354 extending from the tool base 352 and through the cannula 214, with the end effector 222 disposed at the distal end.

Additionally, the tool carriage 320 may actuate a set of articulated movements of the end effector, such as through a cable system or wires manipulated and controlled by actuated drives. The tool carriage 320 may include different configurations of actuated drives. For example, the rotary axis drives may include a motor with a hollow rotor and a planetary gear transmission at least partially disposed within the hollow rotor. The plurality of rotary axis drives may be arranged in any suitable manner. For example, the tool carriage 320 may include six rotary drives 322A-322F arranged in two rows, extending longitudinally along the base that are slightly staggered to reduce width of the carriage and increase the compact nature of the tool driver. As shown in FIG. 3B, rotary drives 322A, 322B, and 322C may be generally arranged in a first row, while rotary drives 322D, 322E, and 322F may be generally arranged in a second row that is slightly longitudinally offset from the first row.

Figure 4B:
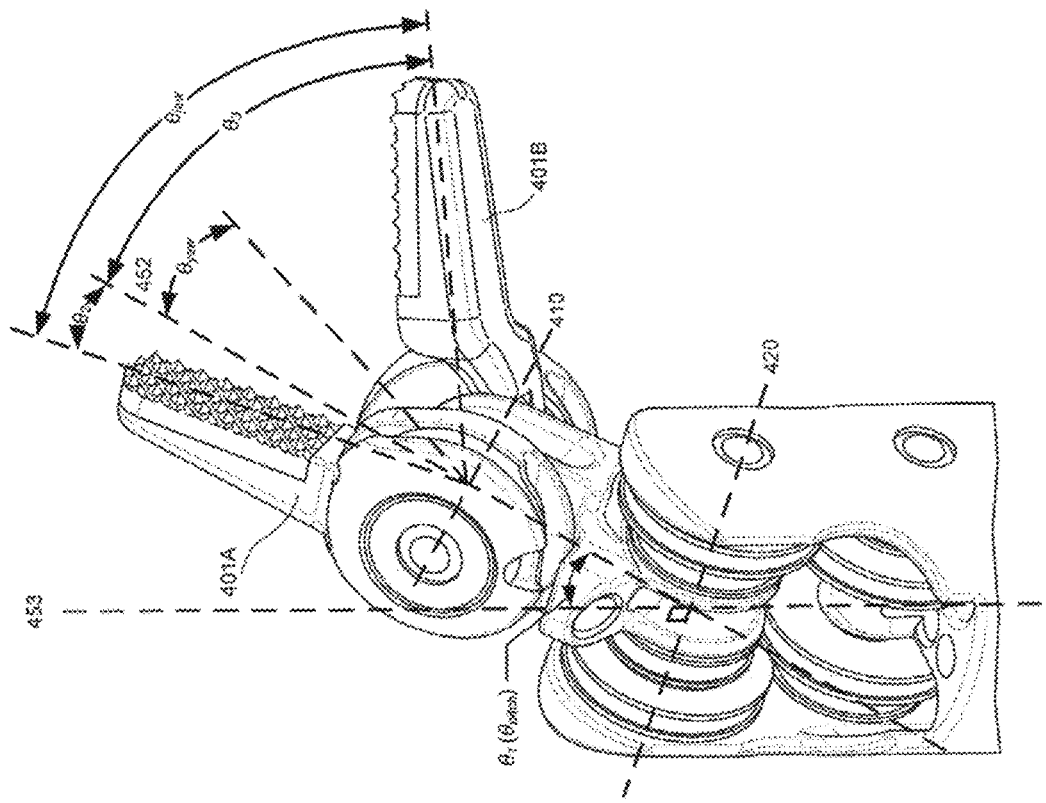
FIGS. 4A and 4B illustrate an end effector of an exemplary grasper having a robotic wrist, a pair of opposing jaws, and a pulley and cable system for coupling the robotic wrist and the pair of jaws to the actuators of a tool driver.
Figure 4A:
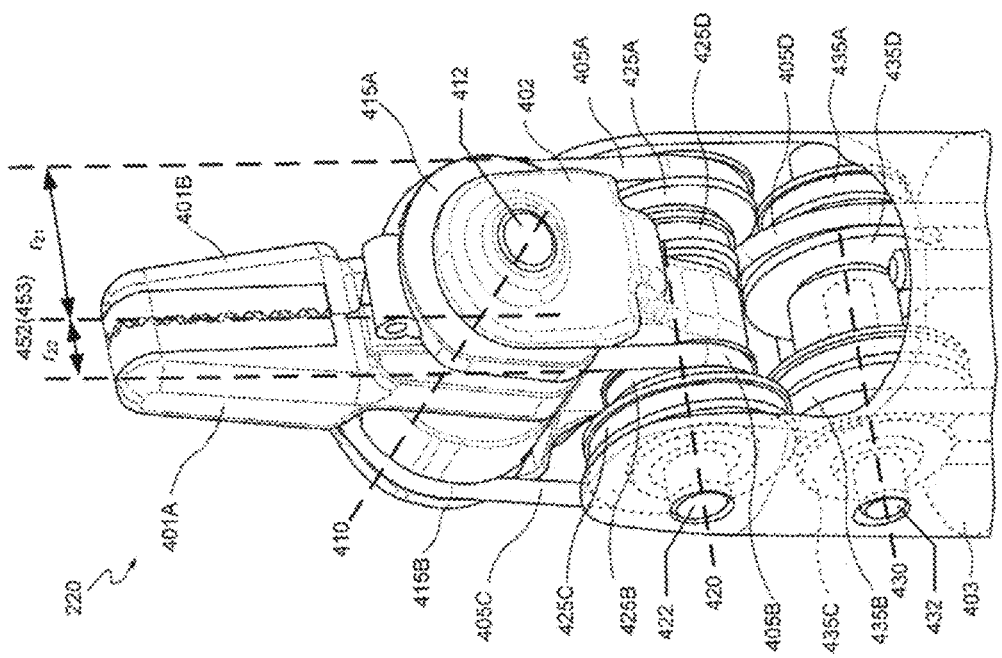

FIGS. 4A and 4B are schematic diagrams illustrating an end effector of an exemplary tool having a robotic wrist, a pair of opposing jaws, and a pulley and cable system for coupling the robotic wrist and the pair of jaws to actuators of a tool driver. Note that although the following tool model and controller design are described with reference to the exemplary surgical robotic grasper, the proposed control system for position and grip force control may be adapted to any tools that include an end effector coupled to a tool shaft via a robotic wrist, which allows multi-axial motion (e.g., pitch and yaw) of the end effector. Similar tools include, but not limited to, needle drivers, monopolar scissors, monopolar hook, bipolar forceps, and other instruments. A needle driver or needle holder includes opposing grippers for holding a needle and operates in a similar manner to the graspers (e.g. open/close, yaw, and pitch) described in detail herein. A set of monopolar scissors are double action scissors with curved plans that also operate in a similar manner to the graspers (e.g. open/close, yaw, and pitch). A set of bipolar forceps includes two tips designed to grasp, manipulate and coagulate selected tissue and also operate in a similar manner to the graspers (e.g. open/close, yaw, and pitch).

As shown in FIG. 4A, the pair of opposing jaws 401A and 401B are movably coupled to a first yoke 402 of the robotic wrist via an extended axle 412 along a first axis 410. The first yoke 402 may be movably coupled to a second yoke 403 of the robotic wrist via a second extended axle 422 along a second axis 420. The pair of jaws 401A and 401B may each be coupled or integrally formed with pulleys 415A and 415B respectively, via the extended axle 412, so that both jaws can rotate about the axis 410. Pulleys 425A, 425B, 425C and 425D are coupled to the extended axle 422 and rotate around the axis 420. The pulleys 425A, 425B, 425C and 425D are arranged into a first set of pulleys 425B and 425C on one side of the yoke 402 and a second set of pulleys 425A and 425D on the other side of the yoke 402. The pulleys 425A and 42C are outer pulleys and the pulleys 425B and 425D are inner pulleys. Similarly, the third set of pulleys 435A, 435B, 435C and 435D are coupled to a third extended axle 432 and rotate around the axis 430, which is parallel to the axis 420.

The end effector 222 (grasper) can be actuated to move one or both of the jaws 401A and 401B in a variety of ways around the axis 410. For example, the jaws 401A and 401B may open and close relative to each other. The jaws 401A and 401B may also be actuated to rotate together as a pair to provide a yaw motion of the end effector 222 (grasper). In addition, the first yoke 402, the pulleys 415A and 415B, and the jaws 401A and 401B can rotate about the axis 420 to provide a pitch motion of the end effector 222 (grasper). The motion of the robotic wrist and/or the jaws of the tool can be affected by controlling four independent cables 405A-405D. As shown in FIG. 4A, cable 405A may start (or terminates) from one side of the pulley 415A and route along pulleys 425A and 435A, and cable 405B is configured to terminate at the other side of the pulleys 415A and route through pulleys 425B and 435B. Similarly, another pair of cables 405C and 405D can be coupled to the jaw 401B. For example, cable 405C extends from one side of the pulley 415B to pulleys 425C and 435C; and cable 405D routes through pulleys 425D and 435D and terminates at the other side of pulley 415B. The third set of pulleys 435A, 435B, 435C and 435D are arranged in such a way as to keep the cables 405A-405D affixing to the second set of pulleys 425A-425D and prevent the cables from slipping or sliding relative to the pulleys 425A-425D.

Controlling the motions of the end effector 222 (grasper) via four independent cables has several advantages. One advantage may be the reduction of the number of cables that extend from the tool base 352 to the robotic wrist compared to typical on-market designs using six cables (or three cable loops with six cable ends). Less number of cables can reduce the tool size as well as complexity of the wrist assembly, which may benefit minimally-invasive surgical procedures or non-surgical applications. Furthermore, arrangement of four independent cables instead of two or three cable loops not only allows independent control of the tension on each cable without the need for pre-tensioning of the cables, but also enables variable compliance in the wrist joints and increased sensitivity to external loads. Additionally, it is possible to readjust tension on each cable independently, which can further increase tool performance.

As shown in FIGS. 4A and 4B, the end effector 222 (grasper) can be actuated to move the jaws 401A and 401B in a variety of ways such as grasping (e.g., jaws rotating independently about axis 410), yaw (e.g., jaws rotating together about axis 410), and pitch (e.g., jaws rotating about axis 420) by imparting motion to one or more of the pulleys 415A, 415B, 425A, 425B, 425C, and 425D to thereby impart motion on the first yoke 402 and/or one or both of the jaws 401A and 401B. Cables 405A-405D can be grouped into two antagonistic pairs, that is, when one cable of the antagonistic pair is actuated or tensioned, while the other cable is loosened, the jaw will rotate in one direction. Whereas when only the other cable is tensioned, the jaw will rotate in an opposite direction.

For example, cables 405A and 405B are the first antagonistic pair for moving jaw 401A, and cables 405C and 405D are the second antagonistic pair for controlling jaw 401B. When cable 405A is tensioned (e.g., by at least one of the rotary drives 322A-322F) while cable 405B is loosened, jaw 401A closes (moving towards the opposite jaw 401B). On the other hand, when cable 405B is tensioned and cable 405A is loosened, jaw 401A opens (moving away from the opposite jaw 401B). Similarly, when tensioned, cable 405C closes jaw 401B (moving towards the opposite jaw 401A) and cable 405D opens jaw 401B (moving away from the opposite jaw 401A) while the other cable loosens. As another example, grip force between the jaw 401A and jaw 401B can be achieved by continuing to tension both cable 405A and cable 405C (while cable 405B and cable 405D are loosened) after the jaws are closed (touching each other).

In case when both cables of an antagonistic pair are tensioned at the same time while both cables of the other pair are loosened, the pulley 415A or pulley 415B do not rotate. Instead, the first yoke 402 together with the jaws 401A and 401B are imparted by the pulleys 415A and 415B to pitch about the axis 420. For example, when the pair of cables 405A and 405B are both tensioned simultaneously while the pair of cable 405C and 405D are loosened, the jaws (together with the yoke 402) pitch out of the plane of the paper. Whereas when both cables 405C and 405D are tensioned simultaneously and the pair of cables 405A and 405B are kept loose, the jaws pitch into the plane of the paper.

FIG. 4B is a schematic diagram illustrating example angle definitions for various motions of the end effector 221 (grasper). The angles are defined in reference to axes 410 and 420, as well as an axis 452 of the first yoke 402 and an axis 453 of the second yoke 403. For example, as shown in FIG. 4B, an angle ($\theta_1$) between axis 452 and the axis 453 may represent the rotation angle of the yoke 402 around axis 420, which may also be defined as the pitch angle ($\theta_{pitch}$) of the end effector 222 (grasper) (while in FIG. 4A, the axis 452 of the yoke 402 is superimposed over the axis 453 of the yoke 403 because the jaws are staying in the reference position, i.e., no pitch motions). In addition, angles ($\theta_2$) and ($\theta_3$) can represent the angles between each of the jaws 401A and 401B and the axis 452 of the yoke 402 (as the origin), respectively. To differentiate the sides of the axis 452, angles ($\theta_2$) and ($\theta_3$) may take on different signs. For example, angle ($\theta_2$) is negative and angle ($\theta_3$) is positive, as illustrated in FIG. 4B.

In order to perform control tasks, it is often beneficial to define a consistent coordinate frame for the joint angles. For example, the jaw angle ($\theta_{jaw}$) may be defined as the angle between the two jaws 401A and 401B, and the yaw angle ($\theta_{yaw}$) may be defined as the angle between the axis 452 and the line bisecting the jaw angle. These angles may be defined according to Equations 1-3:

$$\theta_{pitch} = \theta_1 \qquad \text{Eq. 1}$$

$$\theta_{yaw} = \tfrac{1}{2}(\theta_2 + \theta_3) \qquad \text{Eq. 2}$$

$$\theta_{jaw} = \theta_2 - \theta_3 \qquad \text{Eq. 3}$$

The transformation between angles in FIG. 4B and the defined angles are as described in Equation 4:

$$\begin{bmatrix} \theta_{pitch} \\ \theta_{yaw} \\ \theta_{jaw} \end{bmatrix} = \begin{bmatrix} 1 & 0 & 0 \\ 0 & 1/2 & 1/2 \\ 0 & 1 & -1 \end{bmatrix} \begin{bmatrix} \theta_1 \\ \theta_2 \\ \theta_3 \end{bmatrix} \qquad \text{Eq. 4}$$

Figure 5:
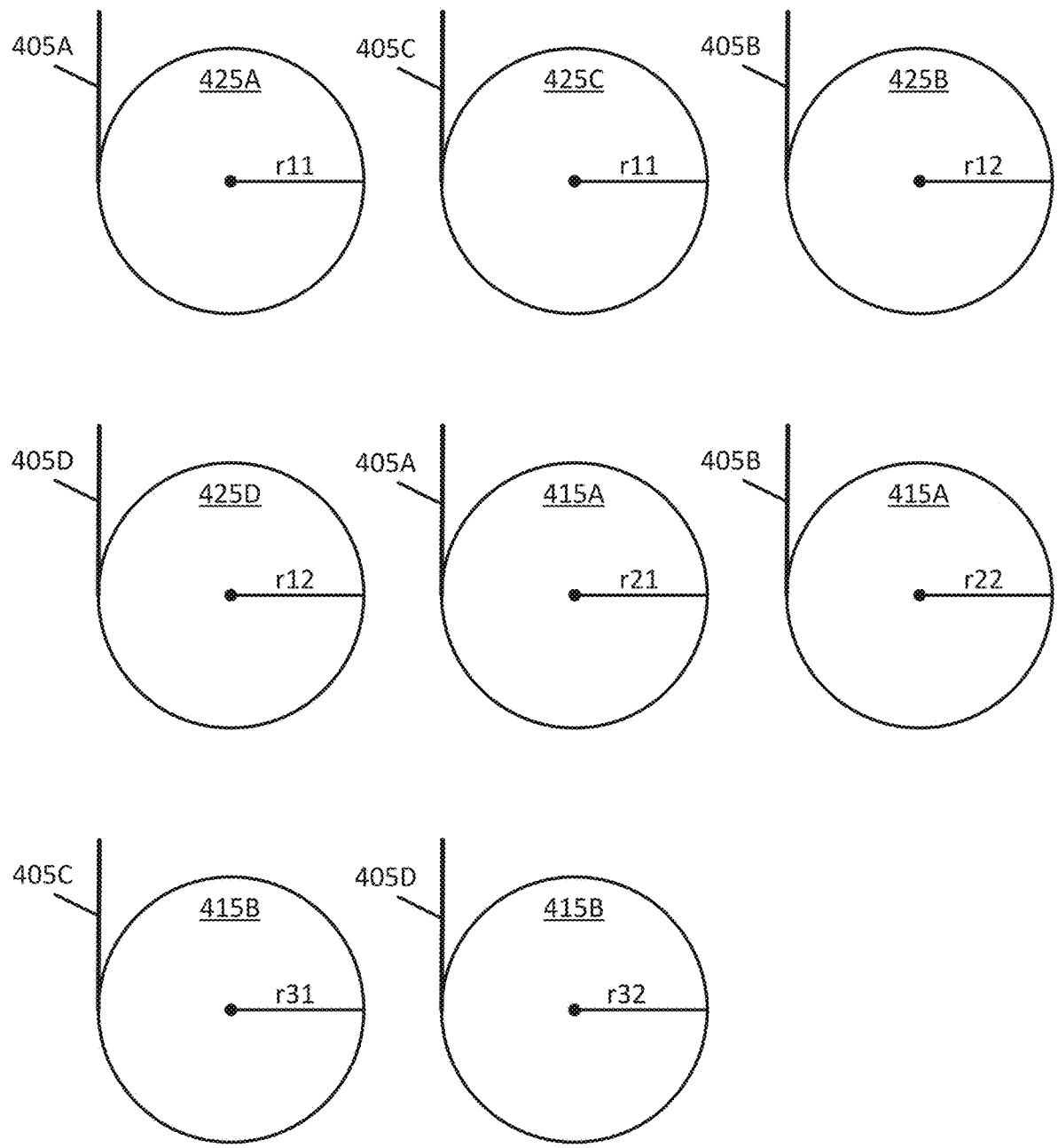
FIG. 5 illustrates pulleys of the pulley and cable system of FIGS. 4A and 4B.

FIG. 5 illustrates pulleys of the pulley and cable system of FIGS. 4A and 4B according to the following nomenclature can be established for pulley geometries:
a) r11 is the radius of the outer pulleys 425A and 425C on which cables 405A and 405C are residing, respectively;
b) r12 is the radius of the inner pulleys 425B and 425D on which cables 405B and 405D are residing, respectively (r11 may or may not be equal to r12);
c) r21 is the radius of pulley 415A on the side that cable 405A is residing (with reference to the center of pulley 415A and axle 412 as shown in FIG. 4A);
d) r22 is the radius of pulley 415A on the side that cable 405B is residing (with reference to the center of pulley 415A and axle 412 as shown in FIG. 4A);
e) r31 is the radius of pulley 415B on the side that cable 405C is residing; and
f) r32 is the radius of pulley 415B on the side that cable 405D is residing.

While in the above example symmetrical design, r31=r21, r32=r22 and r21 (as shown in FIG. 4A), in some other designs it is possible to have r31=r21=r32=r22, as wells as r11=r12.

The fundamental equation that relates cable tensions ($\xi[4\times1]$) or the forces in the cables ($F[4\times1]$) to joint torques ($\tau[3\times1]$) is presented by Equation 5:

$$\tau[3\times1] = B[3\times4] \cdot \xi[4\times1] \qquad \text{Eq. 5a}$$

where matrix (B) has the form given by Equation 5b:

$$B = \begin{bmatrix} -r_{11} & -r_{12} & r_{11} & r_{12} \\ -r_{21} & r_{22} & 0 & 0 \\ 0 & 0 & r_{31} & -r_{32} \end{bmatrix} \qquad \text{Eq. 5b}$$

The joint torques may include the pitch joint $\tau_{pitch}$, yaw joint $\tau_{yaw}$, which may be $\tau_{yaw}=\tau_{jaw1}+\tau_{jaw2}$ in the example of FIGS. 4A and 4B, and the cable tensions may be the forces in the cables (F[4×1]), as shown by Eq. 6.

$$\begin{bmatrix} \tau_{pitch} \\ \tau_{jaw1} \\ \tau_{jaw2} \end{bmatrix} = \begin{bmatrix} -r_{11} & -r_{12} & r_{11} & r_{12} \\ -r_{21} & r_{22} & 0 & 0 \\ 0 & 0 & r_{31} & -r_{32} \end{bmatrix} \begin{bmatrix} F_1 \\ F_2 \\ F_3 \\ F_4 \end{bmatrix} \quad \text{Eq. 6}$$

The kinematic relationship that relates the ideal cable displacements (assuming no cable elasticity) and jaw angles are described in Equation 7:

$$q_{[4\times 1]}=B^T_{[4\times 3]}\theta_{[3\times 1]} \quad \text{Eq. 7}$$

Here $q=[q_1\ q_2\ q_3\ q_4]^T$ is the displacement of cables in the ideal case where the cables are rigid. Therefore, the relationships in expanded form are described as Equation(s) 8:

$$q_1=-r_{11}\theta_1-r_{21}\theta_2$$

$$q_2=-r_{12}\theta_1+r_{22}\theta_2$$

$$q_3=+r_{11}\theta_1+r_{31}\theta_3$$

$$q_4=+r_{12}\theta_1-r_{31}\theta_3$$

where $\theta_1$ is the pitch joint angle, and $\theta_2$ and $\theta_3$ are the joint angles of jaw A and jaw B, respectively (see FIG. 3). In reality, the cables may be somewhat elastic, and the cable forces and elongation follow the Hook's law as shown in Equation(s) 9:

$$\xi_1=k(x_1-q_1)$$

$$\xi_2=k(x_2-q_2)$$

$$\xi_3=k(x_3-q_3)$$

$$\xi_4=k(x_4-q_4)$$

where k is cable elasticity (assuming the four cables are similar), and x is the actuator displacements. The actuator displacements then may be related to the joint angles for the end effector 222 in two different coordinate frames.

If the cables cannot be assumed to be elastic, the above equations may be replaced with the nonlinear equation relating the cable elongation and force.

The angular position and grip force of a distal end effector of a robotic surgical instrument. The end effector may include a robotic wrist and a pair of opposing members (e.g., jaws or claws), each being movable between an open position and a closed position actuated by two antagonistic cables. A total of four cables may each be driven by an independent actuator or motor. The control system may include feedback loops involving position and velocity feedback from the actuators and force feedback measured on the four cables, to effect desired position and grip force. In some implementations, the actuator controllers may be running a position plus feedforward current mode. For example, a position controller may drive the distal end effector to the desired angular position in space based on the positional feedback, while a grip force controller provides additional feedforward current based on the grip force measured by load cells on the four cables to achieve the desired grip force between the opposing members.

Figure 6:
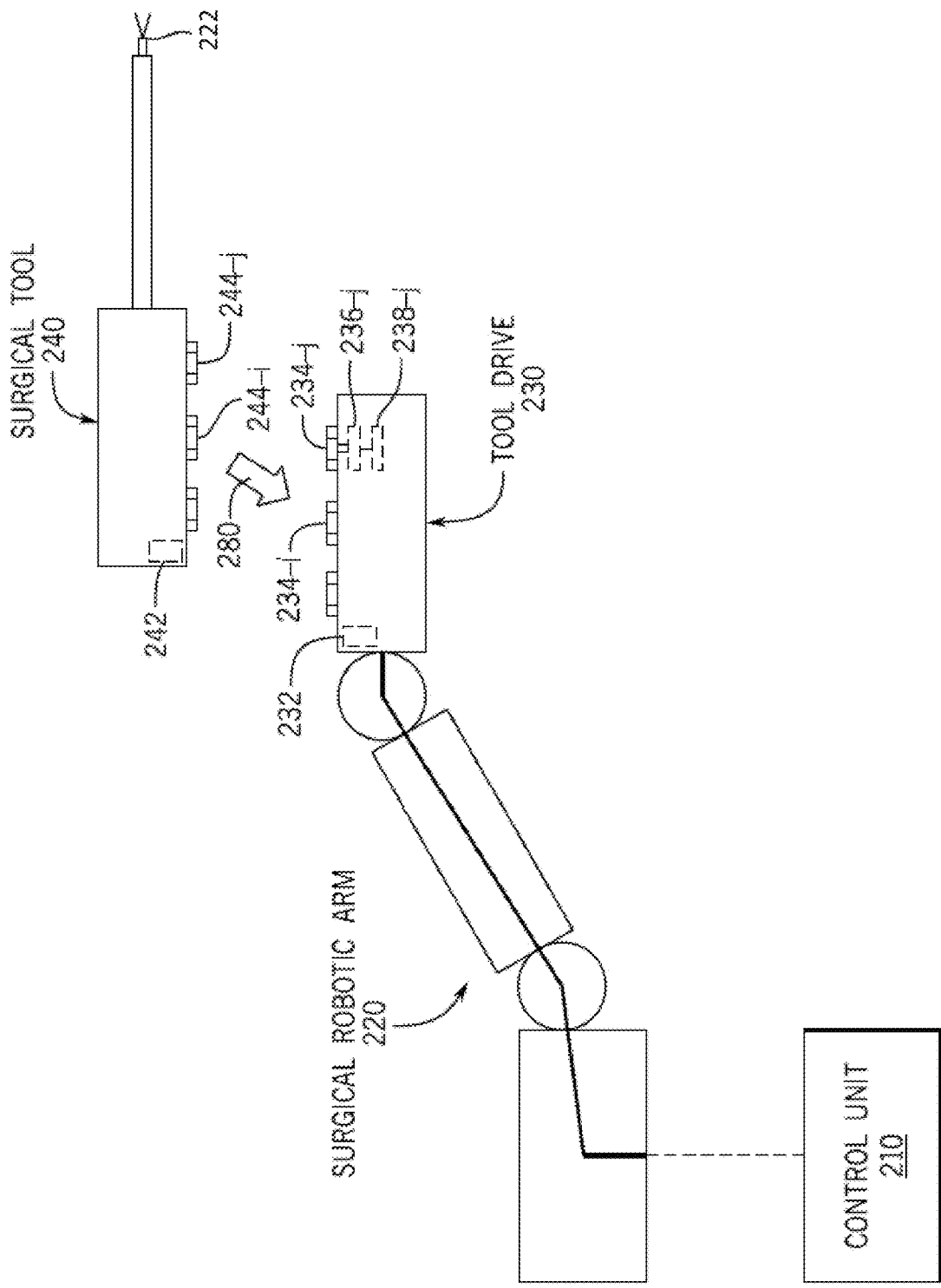
FIG. 6 illustrates a controller for the robotic wrist, tool driver and/or surgical tool.

FIG. 6 is an illustration of a subsystem or a part of the surgical robotic system 100, for detecting engagement of a surgical tool 240 to a tool driver 230 (tool driver) of a surgical robotic arm 122. The surgical robotic arm 122 may be one of the surgical robotic arms of surgical robotic system 100 illustrated and discussed with respect to FIG. 1. The control unit 210 may be part of for example the control tower in FIG. 1. As discussed in more detail herein, the engagement may be detected by control unit 210 based on one or more rotary motor operating parameters of one or more actuators (e.g., actuator 238-j) in the tool driver 230.

There is a tool driver 230 to which different surgical tools (e.g., surgical tool 240, as well as other detachable surgical tools for rotation of an endoscope camera, pivoting of a grasper jaw, or translation of a needle) may be selectively attached (one at a time.) This may be done by for example a human user holding the housing of the surgical tool 240 in her hand and moving the latter in the direction of arrow 280 shown until the outside surface of the surgical tool 240 in which there are one or more tool disks (e.g., tool disk 244-i) comes into contact with the outside surface of the tool driver 230 in which there are one or more drive disks (e.g., drive disk 234-j). The one or more tool disks and/or one or more drive disks may be implemented by pucks, which may be formed of plastic or another durable material. In the example shown, the tool driver 230 is a segment of the surgical robotic arm 122 at a distal end portion of the surgical robotic arm 122. A proximal end portion of the arm is secured to a surgical robotic platform, such as a surgical table that shown in FIG. 1 described above.

Control unit 210 is configured to control motion of the various motorized joints in the surgical robotic arm 122 (including the drive disks 234) through which operation of end effector 222 (its position and orientation as well as its surgical function such as opening, closing, cutting, applying pressure, etc.) which mimics that of a user input device is achieved. This is achieved via a mechanical transmission in the surgical tool 240, when the surgical tool 240 has been engaged to transfer force or torque from the tool driver 230. The control unit 210 may be implemented as a programmed processor, for example as part of the control tower 130 of FIG. 1. It may respond to one or more user commands received via a local or remote user input (e.g., joystick, touch control, wearable device, or other user input device communicating via console computer system.) Alternatively, the control unit 210 may respond to one or more autonomous commands or controls (e.g., received form a trained surgical machine learning model that is being executed by the control unit 210 or by the console computer system), or a combination thereof. The commands dictate the movement of robotic arm 122 and operation of its attached end effector 222.

An end effector 222 may be any surgical instruments, such as jaws (e.g., as shown in FIGS. 4A and 4B), a cutting tool, an endoscope, spreader, implant tool, etc. Different surgical tools each having different end effectors can be selectively attached (one at a time) to robotic arm 122 for use during a surgical or other medical procedure. The end effector 222 depicted in the example of FIG. 5 is jaws located at a distal end of the surgical tool 240 and that may be retracted into, or extend out of, a cannula as shown (e.g., a thin tube that may be inserted into a patient undergoing a surgical procedure).

The robotic arm 122 includes a tool driver 230, in which there are one or more actuators, such as actuator 238-j. Each actuator may be a linear or rotary actuator that has one or more respective electric motors (e.g., a brushless permanent magnet motor) whose drive shaft may be coupled to a respective drive disk 234-j through a transmission (e.g., a gear train that achieves a given gear reduction ratio). The tool driver 230 includes one or more drive disks 234 that may be arranged on a planar or flat surface of the tool driver 230, wherein the figure shows several such drive disks that are arranged on the same plane of the flat surface. Each drive disk (e.g., drive disk 234-*j*) is exposed on the outside surface of the tool driver 230 and is designed to mechanically engage (e.g., to securely fasten via snap, friction, or other mating features) a mating tool disk 244-*j* of the surgical tool 240, to enable direct torque transfer between the two. This may take place once for example a planar or flat surface of the surgical tool 240 and corresponding or mating planar or flat surface of the tool driver 230 are brought in contact with one another.

Furthermore, a motor driver circuit (for example, installed in the tool driver 230 or elsewhere in the surgical robotic arm 122) is electrically coupled to the input drive terminals of a constituent motor of one or more of the actuators 238. The motor driver circuit manipulates the electrical power drawn by the motor in order to regulate for example the speed of the motor or its torque, in accordance with a motor driver circuit input, which can be set or controlled by control unit 210, which results in the powered rotation of the associated drive disk (e.g., drive disk 234-*j*).

When the mating drive disk 234-*j* is mechanically engaged to a respective tool disk 244-*j*, the powered rotation of the drive disk 234-*j* causes the tool disk 244-*j* to rotate, e.g., the two disks may rotate as one, thereby imparting motion on, for example, linkages, gears, cables, chains, or other transmission devices within the surgical tool 240 for controlling the movement and operation of the end effector 222 which may be mechanically coupled to the transmission device.

Different surgical tools may have different numbers of tool disks based on the types of movements and the number of degrees of freedom in which the movements are performed by their end effectors, such as rotation, articulation, opening, closing, extension, retraction, applying pressure, etc.

Furthermore, within the surgical tool 240, more than one tool disk 244 may contribute to a single motion of the end effector 222 to achieve goals such as load sharing by two or more motors that are driving the mating drive disks 234, respectively. In another aspect, within the tool driver 230, there may be two or more motors whose drive shafts are coupled (via a transmission) to rotate the same output shaft (or drive disk 234), to share a load.

In yet another aspect, within the surgical tool 240, there may be a transmission which translates torque from two drive disks 234 (via respective tool disks 244) for performing complementary actions in the same degree of freedom, e.g., a first drive disk 234-*j* rotates a drum within the housing of the surgical instrument 240 to take in one end of a rod, and a second drive disk 234-*i* rotates another drum within the housing of the surgical instrument 240 to take in the other end of the rod. As another example, the extension and the shortening of an end effector along a single axis may be achieved using two tool disks 234-*i*, 234-*j*, one to perform the extension and another to perform the retraction. This is in contrast to an effector that also moves in one degree of freedom (e.g., extension and shortening longitudinally along a single axis of movement) but that only needs a single tool disk to control its full range of movement. As another example, an effector that moves in multiple degrees of freedom (e.g., such as a wristed movement, movement along multiple axes, activation of an energy emitter in addition to end effector movement, etc.) may necessitate the use of several tool disks (each being engaged to a respective drive disk). In another type of surgical tool 240, a single tool disk 244 is sufficient to perform both extension and retraction motions, via direct input (e.g., gears). As another example, in the case of the end effector 222 being jaws, two or more tool disks 244 may cooperatively control the motion of the jaws, for load sharing, as discussed in greater detail herein.

In yet another aspect, within the surgical tool 240, there may be a transmission which translates torque from two drive disks 234 (via respective tool disks 244) for performing complementary actions in the same degree of freedom, e.g., a first drive disk 234-*i* rotates a drum within the housing of the surgical tool 230 to take in one end of a cable, and a second drive disk 234-*j* rotates another drum within the housing of the surgical tool 230 to take in the other end of the cable. As another example, the extension and the shortening of an end effector along a single axis may be achieved using two tool disks 234-*i*, 234-*j*, one to perform the extension and another to perform the retraction, for example via different cables. This is in contrast to an effector that also moves in one degree of freedom (e.g., extension and shortening longitudinally along a single axis of movement) but that only needs a single tool disk to control its full range of movement. As another example, an effector that moves in multiple degrees of freedom (e.g., such as a wristed movement, movement along multiple axes, activation of an energy emitter in addition to end effector movement, etc.) may necessitate the use of several tool disks (each being engaged to a respective drive disk). In another type of surgical tool 240, a single tool disk 244 is sufficient to perform both extension and retraction motions, via direct input (e.g., gears). As another example, in the case of the end effector 246 being jaws, two or more tool disks 244 may cooperatively control the motion of the jaws, for load sharing, as discussed in greater detail herein.

Figure 7:
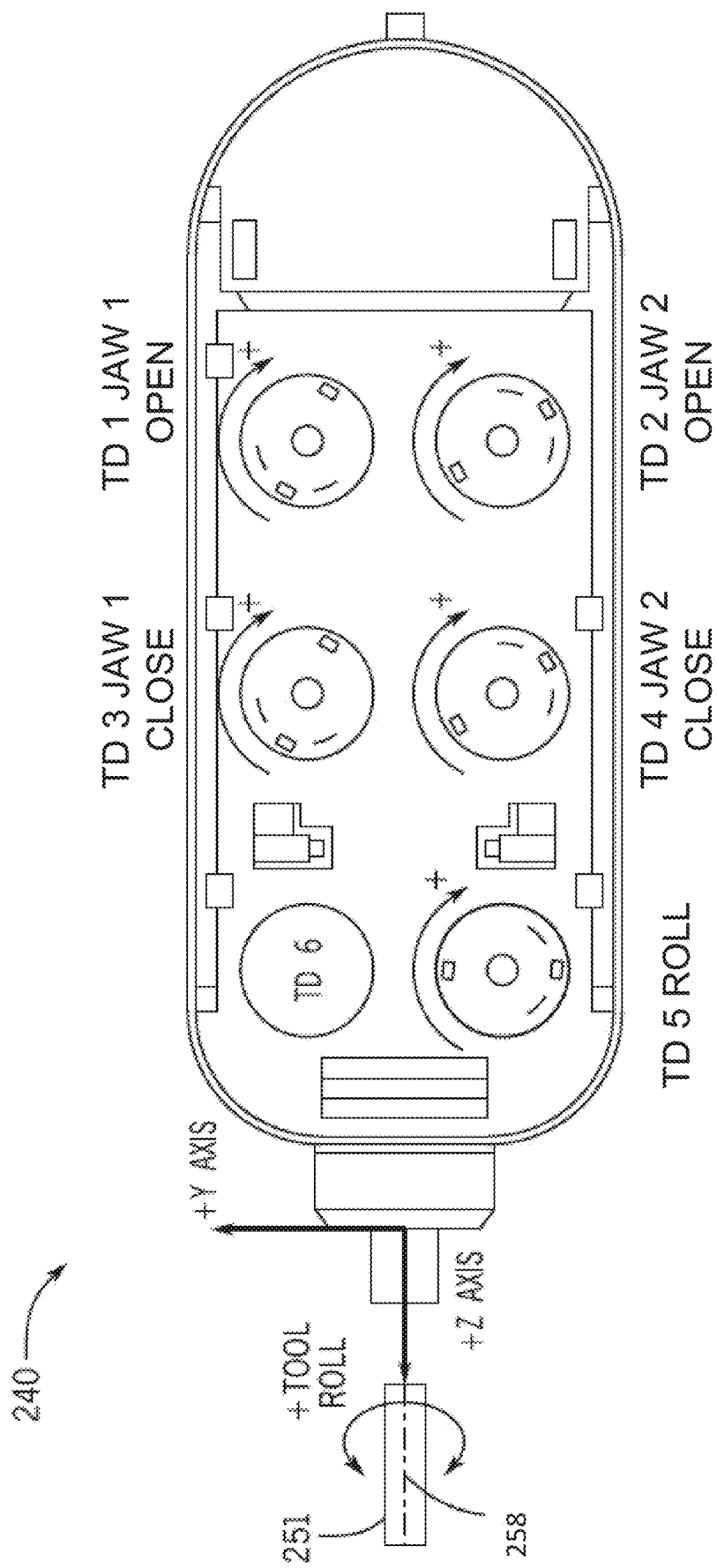
FIG. 7 illustrates a mapping for the tool driver to the surgical tool.

FIG. 7 illustrates an example of the surgical tool 240 including rotary device assignments or mapping for tool disks TD1-5 (TD 6 is unused in this example). In this example, tool disk TD5 is mapped to the roll axis 258 of the end effector, which is illustrated as jaw 251 and may comprise a first opposing jaw 401A and a second opposing jaw 401B. The tool disk TD5 may be coupled to one or more gears that drive the wrist to rotate about the roll axis. Each opposing jaw is assigned two tool disks. For example, the first opposing jaw 401A may be assigned to tool disk TD1 for opening the jaw (i.e., increasing the angle between the first opposing jaw 401A and the second opposing jaw 401B) and tool disk TD3 for closing the jaw (i.e., decreasing the angle between the first opposing jaw 401A and the second opposing jaw 401B). The tool disk TD1 may be coupled to a cable that rotates pulley 415A in a first direction and the tool disk TD3 may be coupled to a cable for rotating pulley 415A in a second direction.

Similarly, the second opposing jaw 401B may be assigned to tool disk TD2 for opening the jaw (i.e., increasing the angle between the first opposing jaw 401A and the second opposing jaw 401B) and tool disk TD4 for closing the jaw (i.e., decreasing the angle between the first opposing jaw 401A and the second opposing jaw 401B). The tool disk TD2 may be coupled to a cable that rotates pulley 415B in a first direction and the tool disk TD4 may be coupled to a cable for rotating pulley 415B in a second direction.

In some embodiments, when surgical tool 240 is first attached to or installed on tool driver 230 such that the tool disks are brought substantially into coplanar and coaxial alignment with corresponding drive disks (though the tool and drive disks are perhaps not yet successfully engaged), control unit 210 initially detects the type of the surgical tool 240. In one embodiment, surgical tool 240 has an information storage unit 242, such as a solid state memory, radio frequency identification (RFID) tag, bar code (including two-dimensional or matrix barcodes), etc., that identifies its tool or end effector information, such as one or more of identification of tool or end effector type, unique tool or end effector ID, number of tool disks used, location of those tool disks being used (e.g., from a total of six possible tool disks 244-*e, f, g, h, i, j*), type of transmission for the tool disks (e.g., direct drive, cable driven, etc.), what motion or actuation a tool disk imparts on the end effector, one or more tool calibration values (e.g., a rotational position of the tool disk as determined during factor testing/assembly of the tool), whether motion of the end effector is constrained by a maximum or minimum movement, as well as other tool attributes. In one embodiment, the information storage unit 242 identifies minimal information, such as a tool ID, which control unit 210 may use to perform a lookup of the various tool attributes.

The tool driver 230 may include a communication interface 232 (e.g., a memory writer, a near field communications, near field communication (NFC), transceiver, RFID scanner, barcode reader, etc.) to read the information from the information storage unit 242 and pass the information to control unit 210. Furthermore, in some embodiments, there may be more than one information storage unit in surgical tool 240, such as one information storage unit associated with each tool disk 244. In this embodiment, tool driver 230 may also include a corresponding sensor for each possible information storage unit that would be present in a given tool.

After surgical tool 240 is attached with tool driver 230, such that tool disks are brought into alignment and are superimposed on corresponding drive disks (although not necessarily mechanically engaged), and after the tool disk information is obtained, e.g., read by control unit 210, the control unit 210 performs an engagement process to detect when all of the tool disks that are expected to be attached to respective drive disks are mechanically engaged with their respective drive disks (e.g., their mechanical engagement has been achieved, or the tool driver 230 is now deemed engaged with the tool). That is, attaching the surgical tool 240 with the tool driver 230 does not necessarily ensure the proper mating needed for mechanical engagement of tool disks with corresponding drive disks (e.g., due to misalignment of mating features). The engagement process may include activating one or more motors of an actuator (e.g., actuator 238-*j*) that drives a corresponding drive disk 234-*j*. Then, based on one or more monitored motor operating parameters of the actuator 238-*j*, while the latter is driving the drive disk 234-*j*, the mechanical engagement of the tool disk 244-*i* with a drive disk 234-*j* can be detected. This process may be repeated for every drive disk 234 (of the tool driver 230) that is expected to be currently attached to a respective tool disk 244 (e.g., as determined based on the tool disk information obtained for the particular surgical tool 240 that is currently attached.)

Upon detecting that a particular type of surgical tool 240 has been attached with the tool driver 230, the control unit 210 activates one or more actuators (e.g., motors) of the tool driver 230 that have been previously associated with that type of surgical tool 240. In some embodiments, each actuator that is associated with a corresponding drive disk 234 of surgical tool 240 may be activated simultaneously, serially, or a combination of simultaneous and serial activation.

Figure 8:
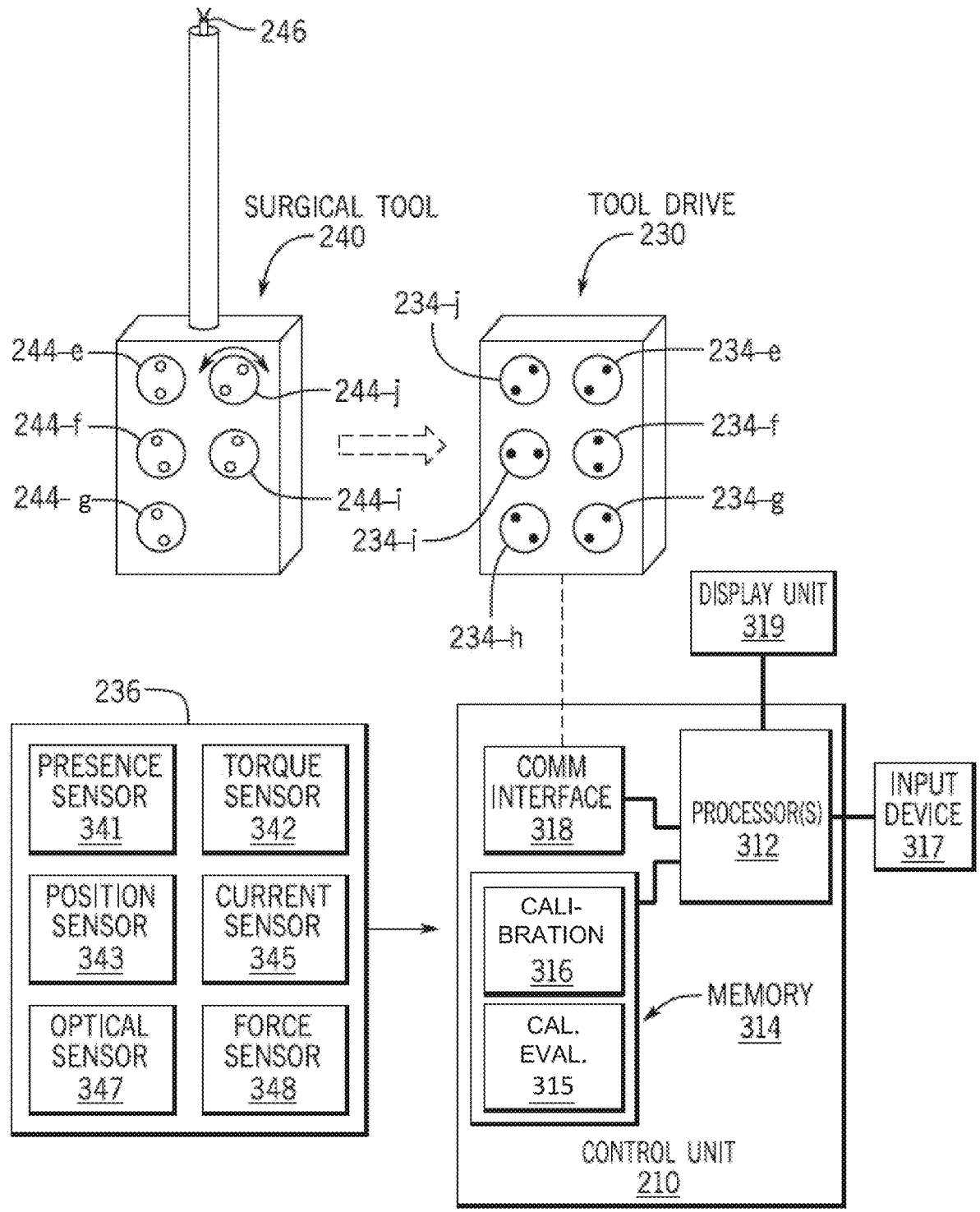
FIG. 8 illustrates a sensor array and a detailed embodiment of the controller.

FIG. 8 illustrates an example of the surgical tool 240 that utilizes five tool disks, such as tool disks 244-*e, f, g, i, j*, arranged in a coplanar fashion on a mating surface of its housing. Each tool disk contributes to at least a portion of the movement and/or activation of end effector 222. Upon detecting the attachment of surgical tool 240 with tool driver 230 (e.g., joining of mating surfaces of the respective housings), control unit 210 (or its processor 312 while executing instructions stored in memory 314) performs a process which determines that only the corresponding five drive disks, such as drive disks 234 *e, f, g, i, j*, are to be turned (a corresponding actuator 238 is activated) to perform the engagement process.

In some embodiments, the motor operating parameters monitored by the control unit 210 (via sensors 236) are interpreted to mean successful mechanical engagement of a tool disk with a drive disk. The control unit 210 is in communication with and receives sensor data from sensor 236 in an example sensor array including any combination of a presence sensor 341, a torque sensor 342, a position sensor 343, an electrical sensor 345, an optical sensor 347, and a force sensor 348. The sensor array may include separate sensors for different degrees of freedom of the surgical tool (e.g., closure joint, roll joint, or other operation of the surgical tool). That is, the sensor array, or one or more sensors thereof, may be repeated for multiple tool disks 244 in the tool driver 230.

The measurements may include measurements of torque applied by the actuator 238-*j* as measured by the torque sensor 342 or the force sensor 348, measurements of current by the electrical sensor 345 supplied to a motor of the actuator 238-*j* when attempting to drive the actuator to move at a certain velocity (e.g., where the sensor 236-*j* may include a current sensing resistor in series with a motor input drive terminal), measurements of electrical impedance by the electrical sensor 345 as seen into the input drive terminals of the motor of the actuator 238 when attempting to drive the motor to move at a certain velocity (e.g., where the sensor 236-*j* may also include a voltage sensing circuit to measure voltage of the motor input drive terminal), speed of the actuator 238-*j* (e.g., where the optical sensor 347 may include a position encoder on an output shaft of the actuator 238-*j* or on a drive shaft of the motor), as well as other parameters referred to here as motor operating parameters. The measurements may include presence data from the presence sensor 341, implied from any sensor in the sensor array 236, or determined from the interaction between the information storage unit 242 and the communication interface 232. The position sensor 343 is illustrated separately but may be implemented using a combination of the presence sensor 341, the torque sensor 342, the electrical sensor 345, the optical sensor 347, and the force sensor 348. In one example, additional sensors of the same type may be used for the position sensor 343.

While monitoring the one or more motor operating parameters of a particular actuator, when one or more of these parameters satisfies (e.g., meets or reaches) a predetermined condition or threshold, the detection of such a situation can be interpreted by control unit 210 as a mechanical engagement event. Note that satisfying the predetermined condition may for example mean that the monitored operating parameter exhibits certain changes, as per the threshold, relative to an operating parameter of another motor that is part of the same actuator 238-*j* or that is part of another actuator 238-*i* which his being controlled by the control unit 210 simultaneously during the engagement detection process.

In some embodiments, detection of certain motor operating parameters during operation of the actuator 238-*j*, such as one or more of i) torque that satisfies (e.g., rises and reaches) a torque threshold, ii) motor current that satisfies (e.g., rises and reaches) a current threshold, iii) impedance that drops below an impedance threshold, iv) motor speed dropping below a motor velocity threshold, or a combination thereof, are used by control unit 210 to determine that mechanical engagement of tool disk 244-*j* to drive disk 234-*j* has occurred. The following are some examples of such a process.

The control unit 210 including its programmed processor 312 may be integrated into the surgical robotic system 100 (FIG. 1) for example as a shared microprocessor and program memory within the control tower 130. Alternatively, the control unit 210 may be implemented in a remote computer such as in a different room than the operating room, or in a different building than the operating arena shown in FIG. 1. Furthermore, control unit 210 may also include, although not illustrated, user interface hardware (e.g., keyboard, touch-screen, microphones, speakers) that may enable manual control of the robotic arm and its attached surgical tool 240, a power device (e.g., a battery), as well as other components typically associated with electronic devices for controlling surgical robotic systems.

Memory 314 is coupled to one or more processors 312 (generically referred to here as a processor for simplicity) to store instructions for execution by the processor 312. In some embodiments, the memory is non-transitory, and may store one or more program modules, including a hardstop detection algorithm 325, a relative tracking algorithm 236 for hardstop handling, an absolute tracking algorithm 237 for hardstop handling, and a jaw catchup algorithm 328 for hardstop handling, whose instructions configure the processor 312 to perform the calibration and calibration evaluation processes described herein. In other words, the processor 312 may operate under the control of a program, routine, or the execution of instructions stored in the memory 314 as part of the calibration algorithm 316 and the calibration evaluation algorithm 315 to execute methods or processes in accordance with the aspects and features described herein. The memory 314 may include one or more settings, coefficient values, threshold values, tolerance values, calibration values for the surgical tool 240 and/or the tool driver 230. These values may be stored in memory 314 as a configuration file, table, or matrix. Some values in the configuration file may be provided by the user, some may be accessed or retrieved based on identifiers of the surgical tool 240 or tool driver 230, and others may be set by the control unit 210.

Figure 9:
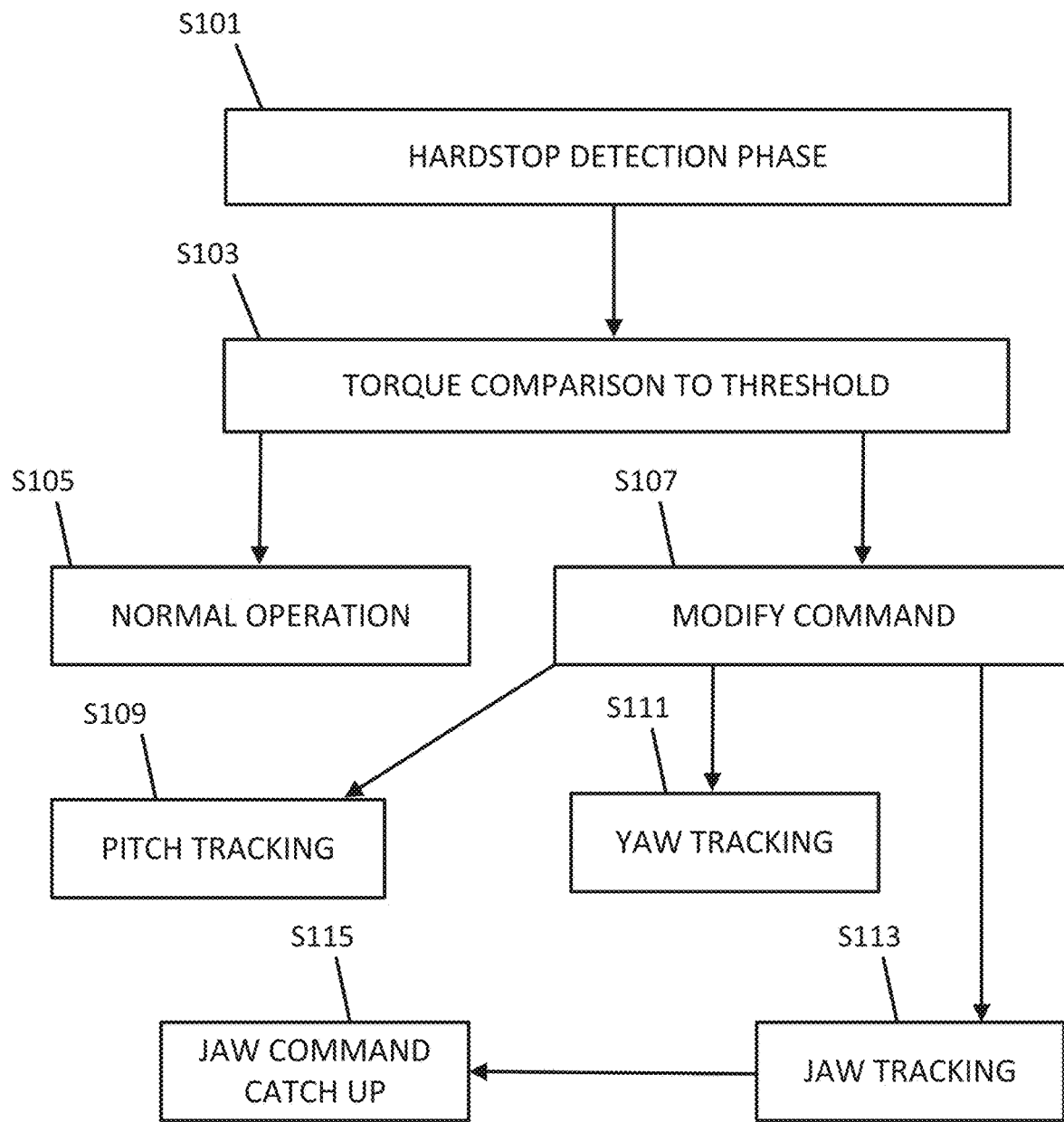
FIG. 9 illustrates an example flow chart for example operations of the controller.

FIG. 9 illustrates a procedure or technique that may be carried out by any of the systems described herein, for example, by a controller, such as the control unit 210. Each act in FIG. 9 may refer to a separate process that may have many steps. The sequence illustrated is only an example and the steps may be performed in any order. Additional, different, or fewer acts may be included.

At S101, a hardstop detection phase is performed. The hardstop may be an obstacle that is contacted by the end effector 222. The hardstop may be defined according to the degree of freedom or axis of the wrist that encounters the hardstop. Thus, the end effector 222 may experience a pitch hardstop when a hardstop is detected in the pitch degree of freedom, a yaw hardstop when a hardstop is detected in the yaw degree of freedom, and/or a roll hardstop when a hardstop is detected in the roll degree of freedom. Opening or closing the jaw may also experience hardstops. These hardstops may be analyzed separately or movement of the jaw may be a factor for the associated axis (e.g., the jaw may contribute to hardstop handling in the yaw axis). The hardstop may be an obstacle contacted within the body of the patient.

As described above, each or one or more of the actuators 238 (motors) may be associated with a sensor such as the torque sensor 342. Respective torque sensors 342 measure the torque on actuators 238. The tension in a cable coupled to the actuator 238 is determined based on the measured torque. The torque on the actuator 238 measured by the torque sensor 342 multiplied by the radius of the actuator 238 and/or radius of the transmission pulley is equal to the tension in the respective coupled cable. As an example, the tensions or cable forces (F1, F2, F3, and F4) may correspond to any order of the cables 405A, 405B, 405C, and 405D, for example in the order of Table 1.

TABLE 1

| Force | Cable |
|-------|-------|
| F1    | 405A  |
| F2    | 405B  |
| F3    | 405C  |
| F4    | 405D  |

The control unit 210 receives values for the cable forces directly from or derived from the data collected at the respective torque sensors 342. The control unit 210 determines which of the cable forces is the greatest. For example, the data in Table 1 may be sorted or each cable force is compared to each other cable force. The control unit 210 selects the highest tensioned cable based on the comparison of forces. The control unit 210 assigned a predetermined value or predetermined force to the selected highest tensioned cable. The predetermined force may have been previously entered by the user (e.g., via input device 317, which may include one or more UIDs) or otherwise stored in memory 314. The predetermined force may be determined from the material properties of the cable or the end effector 222. The predetermined force may be a rated force that can be experienced by the cable before there is a significant risk of the cable breaking or other damage occurring at the end effector 222. The predetermined force may be provided by the manufacturer of the cable. The predetermined force may be determined experimentally through testing the cable or the end effector 222.

At S103, a torque comparison is performed using torque threshold for the joints of the wrist and modified cable forces. A relationship is stored by the control unit 210 that relates the torque of the joint of a wrist to the radius of a pulley and the force of a cable acting on the pulley. The control unit 210 calculates the torque thresholds for a given joint based on at least one modified cable force, which is the predetermined force that is substituted for the selected highest tension cable. For example, the control unit 210 may calculated one or more torque thresholds based on the forces (F1, F2, F3, and F4) associated with the plurality of cables are determined from respective motor torque sensors and associated with pulley dimensions (R11, R12, R21, R22, R31 and R32) for respective pulleys for the cables. The torque thresholds may be considered variable torque thresholds because the values change depending on the measured values from the motor torque sensors. In other words, each of the following torque thresholds change in real time or substantially real time as the forces on the cables change. In each case, one of the force values is held constant, while the others fluctuate according to the data from the motor torque sensors. In each of the following eight scenarios (corresponding to Equations 10a-h) a variable torque threshold for the wrist is based on a sum of the predetermined value for the highest tension cable and detected forces for remaining cables in the remaining cables.

Equation 10a provides a variable wrist torque maximum threshold for the pitch angle $\tau_{pitch}^{max}$ of the wrist. The values F1, F2, and F4 are based on the measured torque values (e.g., from the respective actuators 238). In this case, the cable for F3 corresponds to the selected highest tensioned cable, which means rather than the measured torque value for F3, the predetermined force is substituted as F3'.

$$\tau_{pitch}^{max} = -r11*F1 - r12*F2 + r11*F3' + r12*F4 \quad \text{Eq. 10a}$$

Equation 10b provides a variable wrist torque maximum threshold for the pitch angle $\tau_{pitch}^{max}$ of the wrist. The values F1, F2, and F3 are based on the measured torque values (e.g., from the respective actuators 238). In this case, the cable for F4 corresponds to the selected highest tensioned cable, which means rather than the measured torque value for F4, the predetermined force is substituted as F4'.

$$\tau_{pitch}^{max} = -r11*F1 - r12*F2 + r11*F3 + r12*F4' \quad \text{Eq. 10b}$$

Equation 10c provides a variable wrist torque minimum threshold for the pitch angle $\tau_{pitch}^{min}$ of the wrist. The values F2, F3, and F4 are based on the measured torque values (e.g., from the respective actuators 238). In this case, the cable for F1 corresponds to the selected highest tensioned cable, which means rather than the measured torque value for F1, the predetermined force is substituted as F1'.

$$\tau_{pitch}^{max} = -r11*F1' - r12*F2 + r11*F3 + r12*F4 \quad \text{Eq. 10c}$$

Equation 10d provides a variable wrist torque minimum threshold for the pitch angle $\tau_{pitch}^{max}$ of the wrist. The values F1, F3, and F4 are based on the measured torque values (e.g., from the respective actuators 238). In this case, the cable for F2 corresponds to the selected highest tensioned cable, which means rather than the measured torque value for F2, the predetermined force is substituted as F2'.

$$\tau_{pitch}^{max} = -r11*F1 - r12*F2' + r11*F3 + r12*F4 \quad \text{Eq. 10d}$$

Equation 10e provides a variable wrist torque maximum threshold for the yaw angle $\tau_{yaw}^{max}$ of the wrist. The values F1, F3, and F4 are based on the measured torque values (e.g., from the respective actuators 238). In this case, the cable for F2 corresponds to the selected highest tensioned cable, which means rather than the measured torque value for F2, the predetermined force is substituted as F2'.

$$\tau_{yaw}^{max} = -r21*F1 + r22*F2' + r31*F3 - r32*F4 \quad \text{Eq. 10e}$$

Equation 10f provides a variable wrist torque maximum threshold for the yaw angle $\tau_{yaw}^{max}$ of the wrist. The values F1, F2, and F4 are based on the measured torque values (e.g., from the respective actuators 238). In this case, the cable for F3 corresponds to the selected highest tensioned cable, which means rather than the measured torque value for F3, the predetermined force is substituted as F3'.

$$\tau_{yaw}^{max} = -r21*F1 + r22*F2 + r31*F3' - r32*F4 \quad \text{Eq. 10f}$$

Equation 10g provides a variable wrist torque minimum threshold for the yaw angle $\tau_{yaw}^{min}$ of the wrist. The values F2, F3, and F4 are based on the measured torque values (e.g., from the respective actuators 238). In this case, the cable for F1 corresponds to the selected highest tensioned cable, which means rather than the measured torque value for F1, the predetermined force is substituted as F1'.

$$\tau_{yaw}^{min} = -r21*F1' + r22*F2 + r31*F3 - r32*F4 \quad \text{Eq. 10g}$$

Equation 10h provides a variable wrist torque minimum threshold for the yaw angle $\tau_{yaw}^{min}$ of the wrist. The values F1, F2, and F3 are based on the measured torque values (e.g., from the respective actuators 238). In this case, the cable for F1 corresponds to the selected highest tensioned cable, which means rather than the measured torque value for F1, the predetermined force is substituted as F1'.

$$\tau_{yaw}^{min} = -r21*F1 + r22*F2 + r31*F3 - r32*F4' \quad \text{Eq. 10h}$$

In addition to the selection of the highest tensioned cabled described above, the control unit 210 may select the torque threshold equations based on a comparison of two or more cable forces. For example, when F3>F4, Equation 10a is selected (rather than Equation 10b) for the variable wrist torque maximum threshold for the pitch angle $\tau_{pitch}^{max}$. Otherwise, or when F4>F3, Equation 10b is selected. In another example, when F1>F2, Equation 10c is selected (rather than Equation 10d) for the variable wrist torque minimum threshold for the pitch angle $\tau_{yaw}^{min}$. Otherwise, or when F2>F1, Equation 10d is selected.

In another example, when F2>F3, Equation 10e is selected (rather than Equation 10f) for the variable wrist torque maximum threshold for the yaw angle $\tau_{yaw}^{max}$. Otherwise, or when F3>F2, equation 10f is selected. In another example, when F1>F4, Equation 10g is selected (rather than Equation 10h) for variable wrist torque minimum threshold for the yaw angle $\tau_{yaw}^{min}$. Otherwise, or when F4>F1, equation 10h is selected.

After the variable torque threshold for the wrist is calculated or at specific time intervals as the variable torque threshold for the wrist is calculated, the control unit 210 compares the variable torque threshold to the joint torque calculated based on motor torque measured by the torque sensor on motor or tool driver end.

The control unit 210 may receive data indicative of the torque at the pitch joint $\tau_{pitch}$ and/or data indicative of the torque at the yaw joint $\tau_{yaw}$. The control unit 210 compares the received joint torque to the calculated variable torque threshold(s). When the comparison indicates that the variable wrist torque threshold $\tau_{pitch} < \tau_{pitch}^{min}$ then the wrist is hitting a hardstop on the negative side of a pitch joint of the surgical tool. When the comparison indicates that the variable wrist torque threshold $\tau_{pitch} > \tau_{pitch}^{max}$ then the wrist is hitting a hardstop on the positive side of the pitch joint of the surgical tool. When the comparison indicates that the variable wrist torque threshold $\tau_{yaw} < \tau_{yaw}^{min}$ then the wrist is hitting a hardstop on the negative side of a yaw joint of the surgical tool. When the comparison indicates that the variable wrist torque threshold $\tau_{yaw} > \tau_{yaw}^{max}$ then the wrist is hitting a hardstop on the positive side of the yaw joint of the surgical tool.

For each case, the graphical user interface on the input device 317 may notify the user that the pitch or yaw is hitting the limit, and display instructions to ask the user to move a specific joint angle (e.g., pitch or yaw) closer toward the center position (e.g., homing position), or close the jaw. The notification may include a text message to indicate the direction that is needed to move away from the hardstop. The notification may include a graphical message, for example including an image of the UID, to illustrate the direction that is needed to move away from the hardstop.

At S105, when the torque comparison indicates that none of the variable torque thresholds have been exceeded, the system returns to normal operation. During normal operation, the user commands received at the UID of user input 317 specify one or more positions, wrist angles, or jaw angles for the surgical tool 230 are received at the control unit 210. The control unit 210 calculates the actuator commands necessary to move the wrist and/or jaw to the desired position.

At S107, when the torque comparison indicates that one or more of the variable torque thresholds have been exceeded, any commands received from the user (e.g., via user input 317) are modified in a hardstop handling phase or hardstop handling mode. The variable torque threshold may be exceeded when the joint torque is greater than a maximum torque threshold or when the joint torque is less than a minimum torque threshold. The control unit 210 may activate the hardstop handling mode in response to the comparison indicating that one of the variable torque thresholds has been exceeded. In one example, the hardstop handling mode may be activated when the variable torque threshold has been exceeded for a predetermined amount of time or a predetermined number of samples or comparisons.

In the hardstop handling phase, the control unit 210 receives commands from the user input 317 and modifies those commands depending on the type of hardstop. In one example, the control unit 210 ignores those commands. The hardstop handling phase may include any combination of pitch tracking and handling S109, yaw tracking and handling S111, and jaw tracking and handling S113.

The pitch tracking and handling S109 examples occur when the variable pitch torque threshold is met. That is, when the control unit 210 receives a command to pitch left when the hardstop is detected already at the negative side of the pitch, the control unit 210 will not command the wrist to pitch left. When the hardstop is no longer present, as indicated by the pitch joint torque returning to the acceptable range, the command may be followed to instruct the wrist to pitch left. In some embodiments, the command to pitch left is reduced by a predetermined percentage. Conversely, when the control unit 210 receives a command to pitch right when the hardstop is detected already at the positive side of the pitch angle, the control unit 210 will not command the wrist to pitch right. When the hardstop is no longer present, as indicated by the pitch joint torque returning to the acceptable range, the command may be followed to instruct the wrist to pitch right.

The yaw tracking and handling S111 examples occur when the variable yaw torque threshold is met. When the control unit 210 receives a command to increase the yaw angle of the wrist, but when the hardstop is detected already at the positive direction of yaw, the control unit 210 will not command the wrist to increase the yaw angle. When the hardstop is no longer present, as indicated by the yaw joint torque returning to the acceptable range, the command to increase the yaw angle may be followed. Conversely, when the control unit 210 receives a command to decrease the yaw angle of the wrist, but when the hardstop is detected already at the negative direction of yaw, the control unit 210 will not command the wrist to decrease the yaw angle. When the hardstop is no longer present, as indicated by the yaw joint torque returning to the acceptable range, the command to decrease the yaw angle may be followed.

These examples are summarized in Table 2. Pitch tracking examples are in cases 1 and 2, and yaw tracking examples are cases 3 and 4.

TABLE 2

| | Threshold Exceeded | Hardstop location | HS Handling Phase | If UID is | |
|---|---|---|---|---|---|
| Case 1 | $\tau_{pitch}^{min}$ | Negative side of pitch | Stop decreasing pitch command | Left pitch | $\tau_{pitch} < \tau_{min,\,pitch}$ |
| Case 2 | $\tau_{pitch}^{max}$ | Positive side of pitch | Stop increasing pitch command | Right pitch | $\tau_{pitch} > \tau_{max,\,pitch}$ |
| Case 3 | $\tau_{yaw}^{min}$ | Negative side of yaw | Stop decreasing yaw command | Left yaw | $\tau_{yaw} < \tau_{min,\,yaw}$ |
| Case 4 | $\tau_{yaw}^{min}$ | Positive side of yaw | Stop increasing yaw command | Right yaw | $\tau_{yaw} > \tau_{max,\,yaw}$ |

It should be noted Cases 1-4 are not mutually exclusive. Cases 2 and 4, for example, could be true at the same time. The hardstop handling phase may include simultaneous and independent determinations for all cases.

The jaw handling and tracking S113 may be performed independently or in combination with the pitch tracking and handling S109 and/or the yaw tracking and handling S111. Depending on the particular surgical tool 240 and end effector 222 the angle of the end effector 220 may impact hitting hard stops on another axis such as any combination of pitch, yaw, and roll. For example, turning to FIGS. 4A and 4B when the end effector includes a jaw. The position of the jaw may cause the surgical tool 240 to hit the hardstop. In the example of FIGS. 4A and 4B, the jaw opens about the yaw angle. Thus, opening the jaw may contribute to hitting the hardstop in the yaw direction.

The control unit 210 is configured to receive jaw angle commands from the input device 317. A jaw angle command may indicate a desired angle for the jaw. The jaw angle command may include multiple angle values such as 401 as a first angle for jaw 401A and a second angle for jaw 401B. The jaw angle command may include a value for the difference between the first angle for jaw 401A and the second angle for jaw 401B. The jaw angle may be controlled using an absolute tracking mechanism that map a certain position from the input device 317 to an absolute jaw angle. The input device 317 may include a pressure sensor that determines the user's movement and maps that measurement to the absolute jaw angle.

The hardstop handling phase may include jaw handling when the jaw angle command indicates a nonzero jaw angle. The control unit 210 determines whether a jaw angle has been received from the control unit 317. When a jaw angle has been received, the control unit 210 activates the jaw handling mode, which may be referred to as the jaw handling phase. In another example, the control unit 210 compares the jaw angle to a minimum level (e.g., 5 degrees) and activates the jaw handling mode when the received jaw angle exceeds the minimum level.

Figure 10:
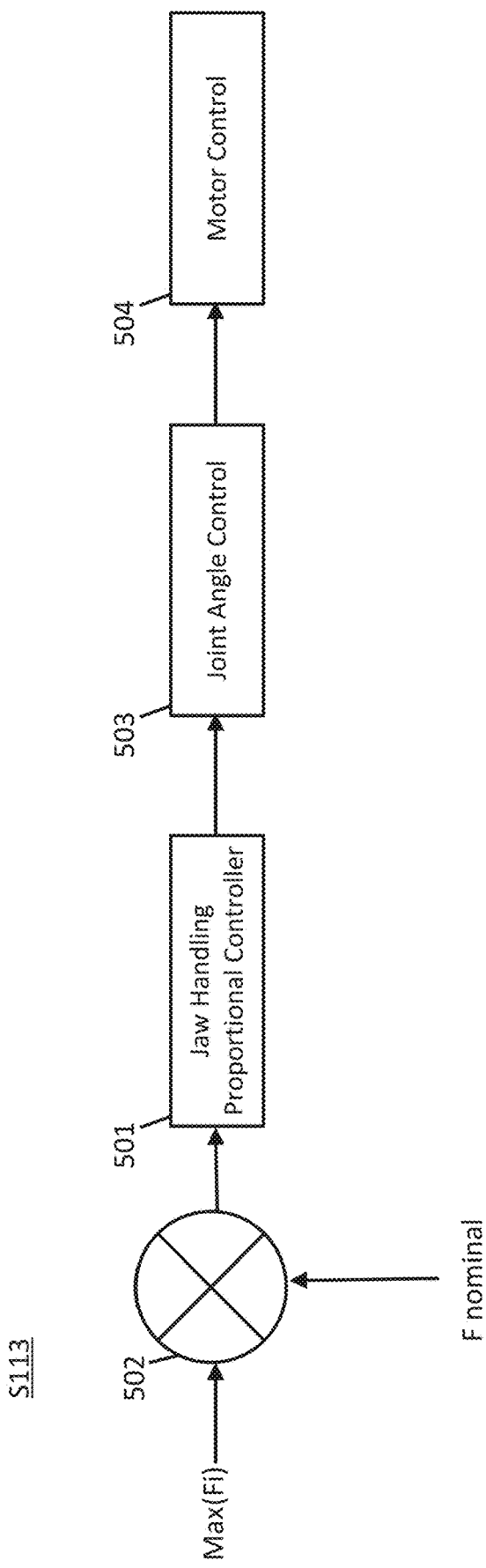
FIG. 10 illustrates an example proportional controller for jaw handling.

The jaw handling mode may be performed by the control unit 210 using a proportional controller. FIG. 10 illustrates an example jaw handling proportional controller 501 for the jaw handling and tracking S113. The jaw handling proportional controller 501 compensates the jaw joint command from the user to protect the cables.

The input of the jaw handling proportional controller 501 includes a force error between the predetermined cable force (e.g., maximum cable force or $F_{nominal}$ such as 140N) and the highest cable force (Max($F_i$)=Max(F1, F2, F3, F4)) from among the four wrist cables, having respective cable forces F1, F2, F3, and F4. Specifically, as implemented by control unit 210, a subtractor 502 may calculate a difference between the Max($F_i$) and $F_{nominal}$. The output of the jaw handling proportional controller 501 is a joint angle control value 503 that is used as the modified joint command for the jaw. The modified joint command may be negative. Because when the hardstop handling has been activated, the highest cable force must be larger than the predetermined value (e.g., 140N). This negative jaw command may be converted into a motor command 504 following inverse kinematic calculation for the robotics wrist control.

Consistent with the earlier hardstop handling phase for pitch and yaw, the jaw handling proportional controller 501 and the jaw tracking and handling phase may be stopped when jaw joint command returns to zero or less than zero. The control unit 210 continues to compare the jaw joint command to zero or the minimum threshold and deactivates the jaw tracking and handling mode when the jaw joint command is equal to zero or less than the minimum threshold. In addition, for the jaw on the yaw axis as shown by FIGS. 4A and 4B, the jaw handling proportional controller 501 and the jaw tracking and handling phase may be stopped when the yaw joint angle returns to the acceptable range (e.g., between $\tau_{yaw}^{min}$ and $\tau_{yaw}^{max}$). The control unit 210 continues to compare the yaw joint angle and deactivates the jaw tracking and handling mode when the jaw joint angle is greater than the $\tau_{yaw}^{min}$ and less than the $\tau_{yaw}^{max}$.

The control unit 210 may perform a jaw command catchup algorithm S115 in response to the jaw handling and tracking S113. When the jaw tracking and handling phase has occurred (e.g., there was a nonzero jaw command received from the user while a corresponding hardstop was detected) and is no longer present, the control unit 210 proceeds to the jaw command catchup phase.

Using the embodiment of FIGS. 4A and 4B as an example, when the yaw torque returns to a nominal value (e.g., between $\tau_{yaw}^{min}$ and $\tau_{yaw}^{max}$), if the jaw handling mechanism was activated previously, there may be a discrepancy between the user's command (e.g., from the input device 317 include UID) for the jaw and the actual jaw command that the motors are following. Therefore, to re-sync the motor command with the UID jaw command and to prevent a sudden jump in jaw position control, the following catching up algorithm for the jaw may be implemented.

In the catching up algorithm, the last joint command output from the Jaw handling P controller may be latched as the initial jaw catching up amount. The control unit 210 may define the initial jaw catching up amount as the last joint command from the joint angle control 503.

The control unit 210 subsequently identifies one or more subsequent UID commands from user input 317 and generates a jaw command adjusted based on the subsequent user input jaw angle.

If the user's UID command for jaw is an increasing angle (i.e., the user is instructing to further open the jaw) or not changing (i.e., the user is instructing to keep current jaw open angle), then the jaw catching up amount will be subtracted from the user's jaw command, and the overall jaw command is used for jaw position control. Thus, the control unit 210 is configured to subtract the initial jaw catching up amount from the subsequent user input jaw angle for a jaw command when the user input jaw angle is to open the jaw.

If the user's UID command for jaw is reducing (i.e., the user is instructing to close the jaw), the jaw catching up amount is reduced by a predefined step size until the total catching up amount is smaller than the predefined step size. This step size is defined to be less than user noticeable jaw movement angle. In this way, the catch up amount will reduce to 0 if the user is closing the jaw for certain time cycles. Thus, the control unit 210 is configured to subtract the predefined step size from the subsequent user input jaw angle for a jaw command when the user input jaw angle is to close the jaw.

The control unit 210 determines whether the catch up amount has reached zero. When the catch up amount has reached zero, the operation routine will return to normal (e.g., the control unit 210 returns to S105).

Figure 11:
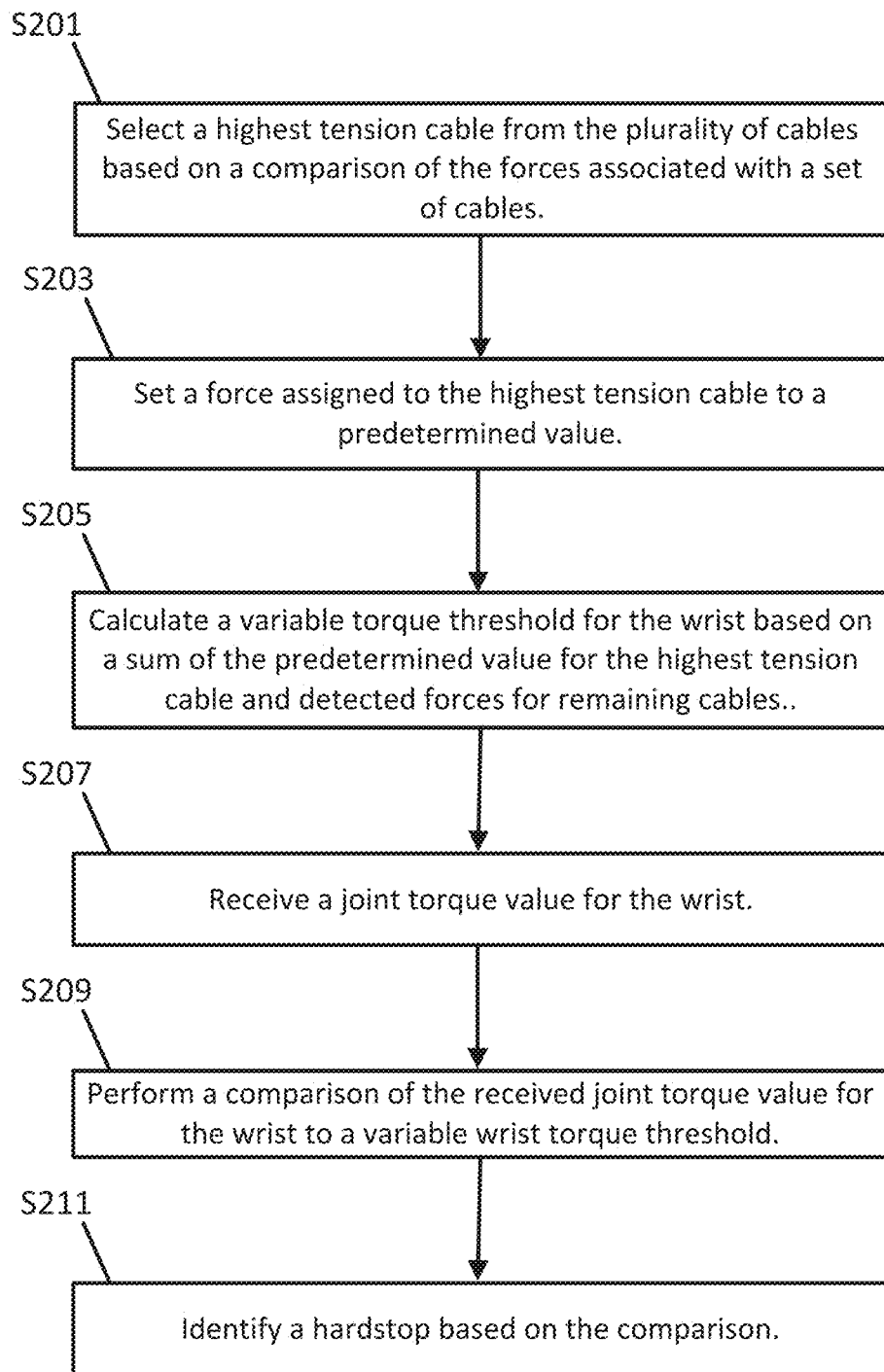
FIG. 11 illustrates an example flow chart for another example operation of the controller

FIG. 11 describes a process for handling one or more hardstops. The process may be performed by a programmed processor (also referred to here as processor or controller), configured according to instructions stored in memory (e.g., the processor 312 and the memory 314 of FIG. 8, where the processor 312 is configured according to the instructions of the calibration control 316 and the calibration evaluation 315). Additional, different, or fewer acts than those in FIG. 11 may be performed.

At act S201, the processor 312 performs a force comparison of the forces associated with a set of cables. The forces may be described in sensor data such as from a force sensor associated with each cable (e.g., force transducer coupled to the cable). The forces may be calculated based on data received from torque sensors coupled to actuators coupled to the respective cables. The processor 312 selects a highest tension cable from the cables based on the comparison of the forces associated with the plurality of cables.

At act S203, the processor 312 sets a predetermined value to the highest tension cable. For example, first the processor 312 selects a highest tensioned cable from the cables based on the comparison of the forces associated with the plurality of cables. Then, the processor 312 sets the force of the highest tensioned cable to a predetermined value. That is, the processor 312 removes or deletes the detected force value for the highest tension cable and replaces it with the predetermined value.

At act S205, the processor 312 calculates a threshold for the wrist based on a sum of the predetermined value for the highest tension cable and detected forces for remaining cables in the plurality of cables. The threshold corresponds to a failure of the highest tensioned cable, represented by the predetermined value, and the threshold fluctuates according to the forces that are being measured for the other cables. The threshold may correspond to any joint of the wrist such as roll, pitch, or yaw.

At act S207, the processor 312 also receives sensor data for the wrist. The sensor data may be generated by a torque sensor coupled to the wrist. A different sensor may be used for each of the joints of the wrist.

At act S209, the processor 312 performs a comparison of the received joint torque value for the wrist to a variable wrist torque threshold. In some examples, the comparison results in an indication (e.g., failure or alert) when the received joint torque value exceeds the variable wrist torque thresholds (e.g., either less than the minimum value when the variable wrist torque threshold is a minimum threshold or greater than the maximum value when the variable wrist torque threshold is a maximum threshold). In some examples, the comparison results in an indication (e.g., failure or alert) when the received joint torque value reaches a predetermined range of the variable wrist torque threshold. The predetermined range may indicate that the threshold is becoming close to being met. In other words, the end effector may have just begun to contact the hardstop. The predetermined range is an indication that the end effector is at risk of hitting the hardstop.

At act S211, the processor 312 identifies a hardstop or risk of hardstop based on the comparison of the received joint torque value for the wrist to the variable wrist torque threshold. When the hardstop is contacted, the processor 312 may instruct the associated actuators 238 to stop or stop increasing or decreasing depending on whether a maximum threshold or a minimum threshold is passed. When the comparison indicates that the received joint torque is within the predetermined range of the threshold, the processor 312 may modify the commands such that one or more velocities of the associated actuators 238 is reduced. The amount of reduction may be calculated in proportion to the difference between the received joint torque value and the variable wrist torque threshold. In either case, an instruction message may be displayed for the user. When the comparison indicates that the received joint torque value returns to the interval between the minimum and maximum for the variable wrist torque threshold, the processor 312 returns the process to normal operation and/or stops modifying commands received from the user.

Herein, the phrase "coupled with" is defined to mean directly connected to or indirectly connected through one or more intermediate components. Such intermediate components may include both hardware- and software-based components. Further, to clarify the use in the pending claims and to hereby provide notice to the public, the phrases "at least one of <A>, <B>, . . . and <N>" or "at least one of <A>, <B>, . . . <N>, or combinations thereof" are defined by the Applicant in the broadest sense, superseding any other implied definitions hereinbefore or hereinafter unless expressly asserted by the Applicant to the contrary, to mean one or more elements selected from the group comprising A, B, . . . and N, that is to say, any combination of one or more of the elements A, B, . . . or N including any one element alone or in combination with one or more of the other elements which may also include, in combination, additional elements not listed.

The disclosed mechanisms may be implemented at any logical and/or physical point(s), or combinations thereof, at which the relevant information/data (e.g., message traffic and responses thereto) may be monitored or flows or is otherwise accessible or measurable, including one or more gateway devices, modems, computers or terminals of one or more market participants, e.g., client computers, etc.

One skilled in the art will appreciate that one or more modules described herein may be implemented using, among other things, a tangible computer-readable medium comprising computer-executable instructions (e.g., executable software code). Alternatively, modules may be implemented as software code, firmware code, specifically configured hardware or processors, and/or a combination of the aforementioned.

The operations of computer devices and systems shown in FIGS. 1-25 may be controlled by computer-executable instructions stored on a non-transitory computer-readable medium. For example, the exemplary computer device or control unit 210 may store computer-executable instructions, generate electronic messages, extracting information from the electronic messages, executing actions relating to the electronic messages, and/or calculating values from the electronic messages to facilitate any of the algorithms or acts described herein. Numerous additional servers, computers, handheld devices, personal digital assistants, telephones and other devices may also be connected to control unit 210.

As illustrated in FIG. 3, the computer system may include a processor 312 implemented by a central processing unit (CPU), a graphics processing unit (GPU), or both. The processor 312 may be a component in a variety of systems. For example, the processor 312 may be part of a standard personal computer or a workstation. The processor 312 may be one or more general processors, digital signal processors, specifically configured processors, application specific integrated circuits, field programmable gate arrays, servers, networks, digital circuits, analog circuits, combinations thereof, or other now known or later developed devices for analyzing and processing data. The processor 312 may implement a software program, such as code generated manually (i.e., programmed).

The computer system includes memory 314 that can communicate via a bus. The memory 314 may be a main memory, a static memory, or a dynamic memory. The memory 314 may include, but is not limited to, computer-readable storage media such as various types of volatile and non-volatile storage media, including but not limited to random-access memory, read-only memory, programmable read-only memory, electrically programmable read-only memory, electrically erasable read-only memory, flash memory, magnetic tape or disk, optical media and the like. In one embodiment, the memory 314 includes a cache or random-access memory for the processor 312. In alternative embodiments, the memory 314 is separate from the processor 312, such as a cache memory of a processor, the system memory, or other memory. The memory 314 may be an external storage device or database for storing data. Examples include a hard drive, compact disk ("CD"), digital video disc ("DVD"), memory card, memory stick, floppy disk, universal serial bus ("USB") memory device, or any other device operative to store data. The memory 314 is operable to store instructions executable by the processor 312. The functions, acts or tasks illustrated in the figures or described herein may be performed by the programmed processor 312 executing the instructions stored in the memory 314. The functions, acts or tasks are independent of the particular type of instructions set, storage media, processor or processing strategy and may be performed by software, hardware, integrated circuits, firmware, microcode and the like, operating alone or in combination. Likewise, processing strategies may include multiprocessing, multitasking, parallel processing and the like.

The computer system may further include a display unit 319, such as a liquid crystal display (LCD), an organic light emitting diode (OLED), a flat panel display, a solid-state display, a cathode ray tube (CRT), a projector, a printer or other now known or later developed display device for outputting determined information. The display 319 may act as an interface for the user to see the functioning of the processor 312, or specifically as an interface with the instructions stored in the memory 314 or elsewhere in the control unit 210.

Additionally, the computer system may include an input device 317 configured to allow a user to interact with any of the components of the system. The input device 317 may be a number pad, a keyboard, or a cursor control device, such as a mouse, or a joystick, touch screen display, remote control or any other device operative to interact with the control unit 210.

The present disclosure contemplates a computer-readable medium that includes instructions or receives and executes instructions responsive to a signal, so that a device connected to a network can communicate voice, video, audio, images or any other data over the network. Further, the instructions may be transmitted or received over the network via a communication interface 318. The communication interface 318 may be a part of the processor 312 or may be a separate component. The communication interface 218 may be a physical connection in hardware. The communication interface 318 is configured to connect with a network, external media, the display unit 319, or any other components in the system, or combinations thereof. The connection with the network may be a physical connection, such as a wired Ethernet connection or may be established wirelessly. Likewise, the additional connections with other components of the system may be physical connections or may be established wirelessly.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the described embodiments should not be understood as requiring such separation in all embodiments, and it should be understood that the described program components and systems can generally be integrated together in a single software product or packaged into multiple software products.

What is claimed is:

1. An apparatus for detecting a hardstop for a surgical tool including a plurality of sensors and a wrist coupled to a plurality of cables, the apparatus comprising:
   one or more processors configured to:
   select a highest tension cable from the plurality of cables based on a comparison of the forces associated with the plurality of cables;
   set a force assigned to the highest tension cable to a predetermined value;
   calculate a variable wrist torque threshold for the wrist based on a sum of the predetermined value for the highest tension cable and detected forces for remaining cables in the plurality of cables; and
   identify a hardstop based on a comparison of a received joint torque value for the wrist to the variable wrist torque threshold.

2. The apparatus of claim 1, the one or more processors configured to:
   when the comparison indicates that the received joint torque value for the wrist exceeds the variable wrist torque threshold, generate a user message with an instruction to move the wrist.

3. The apparatus of claim 2, wherein the instruction to move the wrist include an instruction to move in a yaw direction closer to a home position, an instruction to move in a pitch direction closer to the homing position, or operate an end effector of the wrist.

4. The apparatus of claim 1, wherein the forces (F1, F2, F3, and F4) associated with the plurality of cables are determined from respective motor torque sensors and associated with pulley dimensions (R11, R12, R21, R22, R31 and R32) for respective pulleys for the cables.

5. The apparatus of claim 4, wherein the variable wrist torque threshold for a pitch angle is a minimum pitch angle when one cable is the highest selected cable or a maximum pitch angle when another cable is the highest selected cable.

6. The apparatus of claim 5, wherein when the comparison indicates that the variable wrist torque threshold is less than the minimum pitch angle, then the wrist is hitting a hardstop on a negative side of a pitch joint of the surgical tool; or
   wherein when the comparison indicates that the variable wrist torque threshold is greater than the maximum pitch angle, then the wrist is hitting a hardstop on a positive side of the pitch joint of the surgical tool.

7. The apparatus of claim 4, wherein the variable wrist torque threshold for a yaw angle is a minimum yaw angle when one cable is the highest selected cable or a maximum yaw angle when another cable is the highest selected cable.

8. The apparatus of claim 7, wherein when the comparison indicates that the variable wrist torque threshold is less than the minimum yaw angle, then the wrist is hitting a hardstop on a negative side of a yaw joint of the surgical tool; or
   wherein when the comparison indicates that the variable wrist torque threshold is greater than the maximum yaw angle, then the wrist is hitting a hardstop on a positive side of the yaw joint of the surgical tool.

9. The apparatus of claim 1, the one or more processors configured to:
   activate a hardstop handling phase in response to the comparison of the received joint torque value for the wrist to a variable wrist torque threshold.

10. The apparatus of claim 9, the one or more processors configured to:
    identify a user input wrist angle; and
    provide a motor command independent of the user input angle when the received joint torque value for the wrist exceeds the variable wrist torque threshold.

11. The apparatus of claim 10, the one or more processors configured to:
    provide a second motor command based on the user input angle when the received joint torque value for the wrist does not exceed the variable wrist torque threshold.

12. The apparatus of claim 1, the one or more processors configured to:
 identify a user input jaw angle for a jaw of the surgical tool;
 calculate a force error as a difference between the force assigned to the highest tension cable to the predetermined value; and
 compensate for the force error to modify the user input jaw angle with a proportional control algorithm.

13. The apparatus of claim 12, the one or more processors configured to:
 activate a catching up algorithm for the jaw;
 latch a last joint command from a proportional control algorithm as an initial jaw catching up amount;
 identify a subsequent user input jaw angle to open the jaw or close the jaw; and
 generate a jaw command adjusted based on the subsequent user input jaw angle.

14. The apparatus of claim 13, the one or more processors configured to: subtract the initial jaw catching up amount from the subsequent user input jaw angle for a jaw command when the user input jaw angle is to open the jaw.

15. The apparatus of claim 13, the one or more processors configured to:
 subtract a predefined step size from the subsequent user input jaw angle for a jaw command when the user input jaw angle is to close the jaw.

16. A method for detecting a hardstop for a surgical tool including a plurality of cables, the method comprising:
 select a highest tension cable from the plurality of cables;
 set a force assigned to the highest tension cable to a predetermined value;
 calculate a variable wrist torque threshold for a wrist of the surgical tool based on a sum of the predetermined value for the highest tension cable and detected forces for remaining cables in the plurality of cables; and
 identify a hardstop or a risk of hardstop based on a comparison of a received joint torque value for the wrist to the variable wrist torque threshold.

17. The method of claim 16, wherein the forces (F1, F2, F3, and F4) associated with the plurality of cables are determined from respective motor torque sensors and associated with pulley dimensions (R11, R12, R21, R22, R31 and R32) for respective pulleys for the cables.

18. The method of claim 17, wherein:
 the variable wrist torque threshold is a minimum pitch angle when a first cable or second cable is the highest selected cable; or
 the variable wrist torque threshold is a maximum pitch angle when a third cable or a fourth cable is the highest selected cable; or
 the variable wrist torque threshold is a minimum yaw angle when the first cable or the fourth cable is the highest selected cable; or
 the variable wrist torque threshold is a maximum yaw angle when another cable the second cable or the third cable is the highest selected cable.

19. The method of claim 18, wherein when the comparison indicates that the variable wrist torque threshold is less than the minimum pitch angle, then the wrist is hitting a hardstop on a negative side of a pitch joint of the surgical tool; or
 wherein when the comparison indicates that the variable wrist torque threshold is greater than the maximum pitch angle, then the wrist is hitting a hardstop on a positive side of the pitch joint of the surgical tool; or
 wherein when the comparison indicates that the variable wrist torque threshold is less than the minimum yaw angle, then the wrist is hitting a hardstop on the negative side of a yaw joint of the surgical tool; or
 wherein when the comparison indicates that the variable wrist torque threshold is greater than the maximum yaw angle, then the wrist is hitting a hardstop on the positive side of the yaw joint of the surgical tool.

20. An apparatus for detecting a hardstop for a surgical tool, the apparatus comprising:
 a memory configured to store a maximum cable force for the surgical tool and a set of measured forces associated with a set of cables for the surgical tool;
 a controller configured to determine a highest tensioned cable from the set of measured forces for the set of cables and calculate a variable wrist torque threshold based on the maximum cable force and the set of measured forces,
 wherein the controller compares the variable wrist torque threshold to a received joint torque value for a wrist of the surgical tool and identifies a risk of hardstop is response to the received joint torque value for the wrist exceeding the variable wrist torque threshold.

* * * * *